United States Patent
Herrmann et al.

(10) Patent No.: US 9,738,859 B2
(45) Date of Patent: Aug. 22, 2017

(54) MICROCAPSULES CONTAINING A GAS-GENERATING PHOTOLABILE KETOACID OR KETOESTER AND USES THEREOF

(71) Applicant: FIRMENICH SA, Geneva (CH)

(72) Inventors: Andreas Herrmann, Geneva (CH); Damien Berthier, Geneva (CH); Nicolas Paret, Geneva (CH); Alain Trachsel, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/893,518

(22) PCT Filed: May 20, 2014

(86) PCT No.: PCT/EP2014/060365
§ 371 (c)(1),
(2) Date: Nov. 23, 2015

(87) PCT Pub. No.: WO2014/187833
PCT Pub. Date: Nov. 27, 2014

(65) Prior Publication Data
US 2016/0108346 A1 Apr. 21, 2016

(30) Foreign Application Priority Data
May 22, 2013 (EP) .................................. 13168740

(51) Int. Cl.
| | | |
|---|---|---|
| C11D 3/50 | (2006.01) |
| A61K 8/365 | (2006.01) |
| A61K 8/37 | (2006.01) |
| A61Q 13/00 | (2006.01) |
| A61Q 19/00 | (2006.01) |
| A61K 8/11 | (2006.01) |
| C11D 17/00 | (2006.01) |
| C11B 9/00 | (2006.01) |
| C11D 3/00 | (2006.01) |

(52) U.S. Cl.
CPC ............... *C11D 3/507* (2013.01); *A61K 8/11* (2013.01); *A61K 8/365* (2013.01); *A61K 8/37* (2013.01); *A61Q 13/00* (2013.01); *A61Q 19/00* (2013.01); *C11B 9/00* (2013.01); *C11D 3/001* (2013.01); *C11D 3/505* (2013.01); *C11D 17/0039* (2013.01); *A61K 2800/10* (2013.01); *A61K 2800/56* (2013.01)

(58) Field of Classification Search
CPC . A61K 8/11; A61K 8/365; A61K 8/37; C11D 3/507
See application file for complete search history.

(56) References Cited

U.S. PATENT DOCUMENTS

| | | | |
|---|---|---|---|
| 3,301,439 A * | 1/1967 | Kosar | .................... B01J 13/025 |
| | | | 206/530 |
| 4,396,670 A | 8/1983 | Sinclair | |
| 6,133,228 A * | 10/2000 | Pika | .................... A61K 8/37 |
| | | | 512/21 |
| 6,218,355 B1 * | 4/2001 | Herrmann | ................. A61K 8/37 |
| | | | 424/76.4 |
| 9,334,464 B2 * | 5/2016 | Berthier | .................... B01J 13/06 |
| 2002/0077508 A1 | 6/2002 | Gautschi et al. | |
| 2004/0171516 A1 * | 9/2004 | Derrer | .................... C07C 45/515 |
| | | | 512/24 |
| 2007/0202063 A1 | 8/2007 | Dihora et al. | |
| 2008/0176780 A1 * | 7/2008 | Warr | .................... A61K 8/0237 |
| | | | 510/103 |
| 2013/0230574 A1 * | 9/2013 | Struillou | ................. B01J 13/16 |
| | | | 424/401 |

FOREIGN PATENT DOCUMENTS

| | | |
|---|---|---|
| DE | 15 42 260 A1 | 3/1970 |
| EP | 1 741 775 A1 | 1/2007 |
| GB | 2 432 843 A | 6/2007 |
| GB | 2 432 850 A | 6/2007 |
| GB | 2 432 851 A | 6/2007 |
| GB | 2 432 852 A | 6/2007 |
| WO | 99/60990 A2 | 12/1999 |
| WO | 01/41915 A1 | 6/2001 |
| WO | 02/096850 A1 | 12/2002 |
| WO | 2005/054422 A1 | 6/2005 |
| WO | 2007/062733 A1 | 6/2007 |
| WO | 2007/062833 A1 | 6/2007 |
| WO | 2007/096790 A1 | 8/2007 |
| WO | 2007/135646 A1 | 11/2007 |
| WO | 2008/016684 A1 | 2/2008 |
| WO | 2011/056904 A1 | 5/2011 |
| WO | 2011/154893 A1 | 12/2011 |
| WO | 2011/158962 A2 | 12/2011 |
| WO | 2011/161618 A1 | 12/2011 |
| WO | 2012/104262 A1 | 8/2012 |
| WO | 2013/079435 A1 | 6/2013 |

OTHER PUBLICATIONS

International Search Report and Written Opinion, Appl. No. PCT/EP2014/060365, Jul. 25, 2014.
Böne et al., "Microencapsulated Fragrances in Melamine Formaldehyde Resins," Chimia, 65(3):177-181 (2011).
Herrmann, "Controlled Release of Volatiles under Mild Reaction Conditions: From Nature to Everyday Products," Angew. Chem. Int. Ed., 46(3):5836-5863 (2007).
Lee et al., "Microencapsulation of fragrant oil via in situ polymerization: effects of pH and melamine-formaldehyde molar ratio," Journal of Microencapsulation, 19(5):559-569 (2002).

* cited by examiner

*Primary Examiner* — John Hardee
(74) *Attorney, Agent, or Firm* — Winston & Strawn LLP

(57) ABSTRACT

The present invention relates to water-dispersable microcapsules comprising an oil phase, e.g. a perfume, containing a photolabile α-ketoacid or α-ketoester capable of generating a gas upon exposure to light. The gas is able to cause an extension or the breaking of the microcapsule allowing the release of the oil phase and thus increasing the long-lastingness of the odor perception. The present invention concerns also the use of said microcapsules in perfumery as well as the perfuming compositions or perfumed articles comprising the invention's microcapsules to provide a prolonged release of fragrant molecules.

15 Claims, 4 Drawing Sheets

MICROCAPSULES CONTAINING A GAS-GENERATING PHOTOLABILE KETOACID OR KETOESTER AND USES THEREOF

TECHNICAL FIELD

The present invention relates to water-dispersible microcapsules capable of increasing the long-lastingness of active compounds and of releasing those compounds upon exposure to light. The invention concerns the encapsulation of a photolabile α-ketoacid or α-ketoester capable of releasing a gas, so as to trigger the release of an oil phase containing at least one active compound capable of bringing a benefit or effect into its surrounding environment, and the use of the resulting microcapsules in consumer products.

PRIOR ART

One of the problems faced by the perfume industry lies in the relatively rapid loss of the olfactive benefit provided by odoriferous compounds as a result of their volatility, particularly that of "top-notes". Also, some fragrance ingredients can be unstable in applications of functional perfumery and get lost due to degradation or to rapid evaporation. These problems are often tackled through the use of delivery systems, e.g. capsules containing a perfume, to release the fragrance in a controlled manner.

Encapsulation of the fragrance can at least partially solve the evaporation problem, but many types of microcapsules are known to lose parts of the fragrance during storage, via diffusion through their shells or walls or as a result of the nature of the consumer product into which they are incorporated and which contains surface active ingredients capable of causing leakage of the perfume.

However, to perceive the perfume with such systems, one either needs to mechanically break the microcapsules or to generate a spontaneous leakage of the perfume out of the capsules at the desired time. In the first case, the olfactive experience is limited to scratching episodes, while in the second case one usually encounters problems of performance due to issues related to the limited shelf-life of the consumer product containing the microcapsules.

It is therefore desirable to create new systems capable of solving or at least reducing the above-cited problems and the present invention provides such a solution.

According to the invention, the fragrance is encapsulated within a solid shell or membrane or yet is part of a matrix system together with a compound which is able to cause an extension or the breaking of the microcapsule and thus triggering the olfactive experience without requiring a scratching episode or relying on a leakage phenomenon which is difficult to control.

The same problem applies to many other benefit agents.

We have now been able to establish that the encapsulation of a photolabile compound able to generate a gas inside microcapsules resulted in the desired effect, i.e. the spontaneous extension or breaking of the microcapsule upon exposure to light. This effect is surprising because one might have expected that the unfavorable transparency of the capsule shell or wall to light would have reduced the efficiency of the photoreaction necessary to release the gas.

DESCRIPTION OF THE INVENTION

One object of the present invention is a non-diffusive microcapsule comprising:

A. a core comprising, or even consisting of:
   an oil phase;
   at least one photolabile α-ketoacid or α-ketoester capable of generating, upon exposure to light a gas selected among the group consisting of CO and $CO_2$ and being of formula

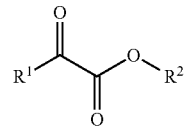

(I)

wherein $R^1$ represents:
   i) a $C_{1-16}$ hydrocarbon group optionally comprising one to four oxygen, sulphur or nitrogen atoms, provided that no heteroatom is directly connected to the CO group; or
   ii) a group of formula $R^{1'}(CO-COOR^2)_n$ wherein $R^2$ has the same meaning as below and $R^{1'}$ is a $C_{2-10}$ hydrocarbon group, optionally comprising one or two oxygen or nitrogen atoms, provided that no heteroatom is directly connected to the CO group, wherein $R^{1'}$ is linked to the keto functional group of the α-ketoacid or α-ketoester and wherein n is an integer comprised between 1 and 4;
and wherein $R^2$ represents either a hydrogen atom or an alkaline metal ion, or a primary or secondary group which is:
   a) a $C_{1-4}$ hydrocarbon group optionally comprising one or two oxygen or nitrogen atoms; or
   b) a $C_{5-22}$ hydrocarbon group optionally comprising one to ten oxygen atoms or one to two nitrogen atoms; provided that said $C_{5-22}$ hydrocarbon group is such as that the corresponding aldehyde or ketone of the O—$R^2$ moiety is an odorless compound; or
   c) a group of formula $R^{2'}(OOC-CO-R^1)_n$ wherein $R^1$ has the same meaning as above and $R^{2'}$ is a $C_{2-12}$ hydrocarbon group optionally comprising one to six oxygen atoms and wherein $R^{2'}$ is linked to the ester functional group of the α-ketoester, and wherein n is an integer comprised between 1 and 4;
   provided that at least one of $R^1$ or $R^2$ is a group as defined in i) or a) or b) respectively; and
   optionally comprising at least one photo-catalyst; and
B. a shell surrounding said core formed by interfacial polymerization, by a phase separation process induced by polymerization or by coacervation.

According to a particular embodiment of the invention, said microcapsule comprises:
A. a core comprising, or even consisting of:
   an oil phase;
   at least one photolabile α-ketoester capable of generating, upon exposure to light a gas selected among the group consisting of CO or $CO_2$ and being of formula

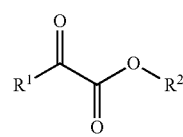

(I)

wherein $R^1$ represents:
  A. a $C_{1-16}$ hydrocarbon group optionally comprising one to four oxygen, sulphur or nitrogen atoms; or
  ii) a group of formula $R^{1'}(CO-COOR^2)_n$ wherein $R^2$ has the same meaning as below and $R^{1'}$ is a $C_{2-10}$ hydrocarbon group and is linked to the ketoester functional group and n is an integer comprised between 1 and 4; and
wherein $R^2$ represents a primary or secondary group which is:
  a) a $C_{1-4}$ hydrocarbon group optionally comprising one or two oxygen or nitrogen atoms;
  b) a $C_{5-22}$ hydrocarbon group optionally comprising one to ten oxygen atoms or one to two nitrogen atoms; provided that said $C_{5-22}$ hydrocarbon group is such as that the corresponding aldehyde or ketone of the O—$R^2$ moiety is an odorless compound; or
  c) a group of formula $R^{2'}(OOC-CO-R^1)_n$ wherein $R^1$ has the same meaning as above and $R^{2'}$ is a $C_{2-12}$ hydrocarbon group optionally comprising one to six oxygen atoms and is linked to the ketoester functional group and n is an integer comprised between 1 and 4;
  provided that at least one of $R^1$ or $R^2$ is a group as defined in i) or a) or b) respectively; and
  optionally comprising at least one photo-catalyst; and
  B. a shell surrounding said core and formed by interfacial polymerization or by a phase separation process induced by polymerization.

Preferably, no heteroatom is directly connected to CO group.

For the sake of clarity, by the expression "microcapsule" or the similar, in the present invention it is meant that the microcapsule comprises an external solid oligomer-based shell or wall and an internal continuous oil phase enclosed by the external shell. In other words, encapsulates such as core-shell systems (e.g. coacervates) or systems with a matrix morphology (e.g. extrudates or porous solid phases containing droplets of a liquid) are considered to be part of the invention. By the expression "core-shell", it is meant that the oil phase is surrounded by a shell whereas by the expression "matrix morphology" it is meant that the oil phase is dispersed in a matrix.

Preferably the microcapsule is a core-shell system.

For the sake of clarity, by the expression "non-diffusive" or the similar in the present invention, it is meant that the shell or wall of the microcapsule is not permeable to the oil phase inside the microcapsule. By the expression "not permeable", it is meant that the release of the oil phase in absence of light shell is negligible or not perceivable (i.e. below the odor threshold).

By the term "oil phase" we mean here a liquid or a solution, at 20° C. and 1 atm of pressure, and which is capable of bringing a benefit or effect into its surrounding environment, and in particular comprises a perfuming, flavoring, cosmetic, skin caring, malodor counteracting, bactericide, fungicide, pharmaceutical or agrochemical ingredient, a diagnostic agent and/or an insect repellent or attractant.

Said oil phase can be composed of a single compound or of a mixture of compounds wherein at least one of the said compounds possesses at least one property which renders it useful as perfuming, flavoring, cosmetic, skin caring, malodor counteracting, bactericide, fungicide, pharmaceutical or agrochemical ingredient and/or as an insect repellent or attractant.

Preferably, said oil phase can be composed of a single compound or of a mixture of compounds wherein at least one of the said compounds possesses at least one property which renders it useful as perfuming, flavoring, cosmetic, skin caring, malodor counteracting, bactericide, fungicide, pharmaceutical or agrochemical ingredient and/or as an insect repellent or attractant.

Practically, the invention is carried out exactly in the same manner, independently of the exact properties of the oil phase. Therefore, it is understood that, even if the invention will be further illustrated herein below with a specific reference to "perfuming" ingredients, the below embodiments are also applicable to other oils (i.e. it is possible to replace the expression "perfuming" with "flavoring", "cosmetic", "skin caring", "malodor counteracting", "bactericide", "fungicide", "pharmaceutical", "agrochemical", "diagnostic agent", "insect attractant" or with "insect repellent" for instance).

For the sake of clarity, by the expression "primary or secondary group", or the similar, in the present invention it is meant that said group is linked to the oxygen atom through a CH or $CH_2$ group, in other words the $R^2$ group is also a group of formula $(R^a)(R^b)CH$ or $(R^a)CH_2$ and the corresponding aldehyde or ketone formed upon exposure to light is of formula $(R^a)(R^b)C=O$ or $(R^a)CHO$.

The reference to the corresponding aldehyde or ketone is important since it is believed that upon exposure to light said photolabile α-ketoester decompose according to the following reaction (herein shown for a secondary group $R^2$):

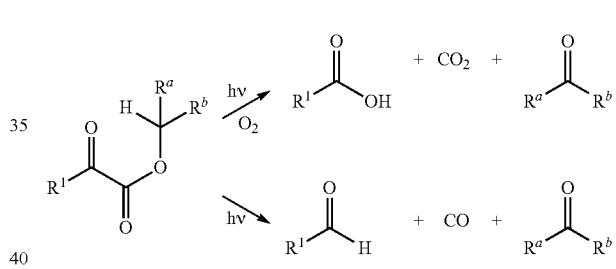

Depending on whether (ambient) oxygen reacts with the reaction intermediate generated upon exposure of a compound of formula (I) to light, a gas being either CO or $CO_2$ or mixtures thereof is formed in addition to the above mentioned aldehyde or ketone.

In the presence or absence of oxygen, α-ketoacids are believed to decompose upon exposure to light in an electron transfer reaction to form $CO_2$.

For the sake of clarity, by the expression "odorless compound", or the similar, in the present invention it is meant that said aldehyde or ketone has a vapor pressure below 2.0 Pa, as obtained by calculation using the program EPI suite (4.0); EPA (US Environmental Protection Agency) and Syracuse Research Corporation (SRC), 2000. Preferably said vapor pressure is below 1.0 Pa, below 0.1 Pa, or even below 0.01 Pa, meaning that said corresponding aldehyde or ketone is not a perfuming one.

It is understood that by " . . . hydrocarbon group . . . " it is meant that said group consists of hydrogen and carbon atoms and can be in the form of a linear, branched or cyclic, aromatic, alkyl, alkenyl, or alkynyl group, e.g., a linear alkyl group, or can also be in the form of a mixture of said type of groups, e.g. a specific group may comprise a linear alkyl, a branched alkenyl (e.g. having one or more carbon-carbon double bonds), a (poly)cyclic alkyl and an aryl moiety, unless a specific limitation to only one type is mentioned.

Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

For the sake of clarity, by the expression "optionally comprising one or several oxygen, sulphur or nitrogen atoms", or the similar, in the present invention it is meant that the group, to which is made reference, may include functional groups such as for examples amines, ethers, thioethers, acetals, esters, aldehydes, ketones, amides, carboxylates or alcohols.

According to a particular embodiment of the invention, the invention's microcapsule is particularly useful when the oil phase comprises a perfuming oil, i.e. a single perfume ingredient or a perfuming composition. A "perfuming ingredient" is a compound, which is of current use in the perfumery industry, i.e. a compound which is used as active ingredient in perfuming preparations or compositions in order to impart a hedonic effect. In other words, such a perfuming ingredient must be recognized by a person skilled in the art of perfumery as being able to impart or modify in a positive or pleasant way the odor of a composition, and not just as having an odor. For the sake of clarity, the definition of a perfuming ingredient is meant to include also compounds that do not necessarily have an odor but are capable of modulating the odor. For the sake of clarity, the definition of perfuming ingredient is meant to include also pro-per-fumes, i.e compounds which upon decomposition liberate a perfuming ingredient. A "perfuming composition" is a mixture of compounds including at least two perfuming ingredients.

In general terms, these perfuming ingredients belong to chemical classes as varied as alcohols, lactones, aldehydes, ketones, esters, ethers, ester nitriles, terpenoids, nitrogenous or sulphurous heterocyclic compounds and essential oils, and said perfuming ingredients can be of natural or synthetic origin. Specific examples of such perfuming ingredients can be found in reference texts such as the book by S. Arctander, "Perfume and Flavor Chemicals", published by the author, Montclair (New Jersey, USA), 1969, or its more recent versions, or in other work of a similar nature, as well as in the abundant patent literature in the field of perfumery. They are well known to the person skilled in the art of perfuming consumer products, that is, of imparting a pleasant odor to a consumer product.

In particular such perfuming oil may comprise also solvents and adjuvants of current use in perfumery.

By "solvents of current use in perfumery" we mean here a material which is practically neutral from a perfumery point of view, i.e. that does not significantly alter the organoleptic properties of perfuming ingredients and is generally not miscible with water, i.e. possesses a solubility in water below 10%, or even below 5%. Solvents commonly used in perfumery, such as for example dipropyleneglycol, diethyl phthalate, isopropyl myristate, benzyl benzoate, 2-(2-ethoxyethoxy)-1-ethanol or ethyl citrate, limonene or other terpenes, isoparaffins such as those known under the trademark Isopar® (origin: Exxon Chemical) or glycol ethers and glycol ether esters such as those known under the trademark Dowanol® (origin: Dow Chemical Company), are suitable solvents for the purposes of the invention.

By "adjuvants of current use in perfumery" we mean here an ingredient capable of imparting additional added benefits such as a color, chemical stability, etc. A detailed description of the nature and type of adjuvant commonly used in perfuming bases cannot be exhaustive, but it has to be mentioned that said ingredients are well known to a person skilled in the art.

Said oil phase can be included at various amounts depending on its nature and the strength of the aimed olfactive effect. Typically, the microcapsules comprise, based on the total microcapsule weight, from about 1% to about 99% by weight, of oil phase. Preferably the microcapsules comprise from about 20% to about 96% of oil phase.

According to any embodiment of the invention, said photolabile α-ketoacid or α-ketoester (herein also referred as "photolabile compound" or simply as "-ketoacid" or "-ketoester") upon decomposition generates a gas together with compounds or residues which are odorless. According to any embodiment of the invention, said photolabile α-ketoacid or α-ketoester is a compound wherein $R^1$ represents:

i) a $C_{1-10}$ hydrocarbon group optionally comprising one or two oxygen, sulphur or nitrogen atoms, provided that no heteroatom is directly connected to the CO group; or ii) a group of formula $R^{1'}(CO—COOR^2)_n$ wherein $R^2$ has the same meaning as above or below and $R^{1'}$ is a $C_{2-6}$ hydrocarbon group and n is equal to 1 or 2.

According to any embodiment of the invention, said $R^1$ represents:

i-a) a $C_{1-6}$ alkyl, alkenyl, cycloalkyl or cycloalkenyl group optionally comprising one or two oxygen or nitrogen atoms, provided that no heteroatom is directly connected to the CO group; or i-b) a phenyl group optionally substituted by one or two $C_{1-4}$ alkyl groups optionally comprising one or two oxygen or nitrogen atoms, provided that no heteroatom is directly connected to the CO group; or ii-a) a group of formula $R^{1'}(CO—COOR^2)_n$ wherein $R^2$ has the same meaning as above or below and $R^{1'}$ is a phenyl group and n is equal to 1 or 2.

According to any embodiment of the invention, said $R^1$ represents:

i-a) a $C_{1-6}$ alkyl, alkenyl, cycloalkyl or cycloalkenyl group, or i-b) a phenyl group optionally substituted by one or two $C_{1-4}$ alkyl groups; or ii-a) a group of formula $R^{1'}(CO—COOR^2)_n$ wherein $R^2$ has the same meaning as above or below and $R^{1'}$ is a phenyl group and n is equal to 1 or 2.

According to any embodiment of the invention, said photolabile α-ketoacid or α-ketoester is a compound wherein $R^2$ represents a hydrogen atom or a primary or secondary group which is:

a) a $C_{2-4}$ hydrocarbon group optionally comprising one or two oxygen or nitrogen atoms; or b) a $C_{5-16}$ hydrocarbon group optionally comprising one to seven oxygen atoms or one or two nitrogen atoms; provided that said $C_{5-16}$ hydrocarbon group is such as that the corresponding aldehyde or ketone of the O—$R^2$ moiety is an odorless compound; or c) a group of formula $R^{2'}(OOC—CO—R^1)_n$ wherein $R^1$ has the same meaning as above and $R^{2'}$ is a $C_{2-6}$ hydrocarbon group optionally comprising one or two oxygen atoms and n is equal to 1 or 2.

According to any embodiment of the invention, said $R^2$ represents a hydrogen atom or a primary or secondary group which is:

a-i) a $C_{2-3}$ hydrocarbon group;

b-i) a $C_{5-10}$ hydrocarbon group optionally comprising one to three oxygen atoms or one or two nitrogen atoms; provided that said $C_{5-16}$ hydrocarbon group is such as that the corresponding aldehyde or ketone of the O—$R^2$ moiety is an odorless compound; or c-i) a group of formula $R^{2'}(OOC$—$CO$—$R^1)$ wherein $R^1$ has the same meaning as above, $R^{2'}$ is a $C_{2-6}$ hydrocarbon group optionally comprising one or two oxygen atoms.

According to any embodiment of the invention, preferred photolabile compounds of formula (I) are those wherein $R^1$ represents a group selected from phenyl, methyl, ethyl, propyl, isopropyl, 2-methylpropyl, n-butyl, 2-butyl, tert-butyl, pentyl, cyclopentyl, hexyl, cyclohexyl, 2-mesityl, 2-furanyl, 2-ethoxy-2-oxoethyl, 2-methoxy-2-oxoethyl, 2-isopropoxy-2-oxoethyl, 2-oxopropyl, 3-ethoxy-3-oxopropyl, 3-methoxy-3-oxopropyl, 3-isopropoxy-3-oxopropyl, 3-oxobutyl, 4-ethoxy-4-oxobutyl, 4-methoxy-4-oxobutyl, 4-isopropoxy-4-oxobutyl and 3,3-dimetyl-2-oxobutyl; even more preferably $R^1$ represents a phenyl group.

According to any embodiment of the invention, preferred photolabile compounds of formula (I) are those wherein $R^2$ represents a group selected from methyl, ethyl and isopropyl and wherein $R^{2'}$ represents a group selected from ethanediyl and propanediyl.

According to any embodiment of the invention, said α-ketoacid or α-ketoester generates a gas upon exposure to light at a wavelength comprised between 450 and 320 nm, preferably between 400 and 320 nm and even more preferably between 380 and 340 nm.

According to any embodiment of the invention, said α-ketoacid or α-ketoester degrades at a rate above $8.0 \times 10^{-5}$ $s^{-1}$, preferably at a rate above $1.0 \times 10^{-4}$ $s^{-1}$, when exposed to UVA-light of 3.1 mW/cm$^2$ at 25° C. for 120 min and at a concentration of 8 mM in acetonitrile. This corresponds to a total energy of ca. 22.3 J/cm$^2$.

According to any embodiment of the invention, said α-ketoacid or α-ketoester is characterized by a calculated log P comprised between 0.5 and 6, preferably between 1.3 and 5, more preferably between 1.5 and 4.5. Said "calculated log P" is the calculated partition parameter of the photolabile compound between octanol and water and can be can be obtained according to the program EPI suite (4.0); EPA (US Environmental Protection Agency) and Syracuse Research Corporation (SRC), 2000.

Said photolabile compound can be included in the microcapsules in various amounts depending on its nature and the speed of release of the oil phase which is aimed. Typically, the microcapsules comprise, based on the total microcapsule weight, from about 1% to about 99.9990% by weight, of photolabile compound. Preferably the microcapsules comprise from about 5% to about 80% of photolabile compound, preferably from 10% to about 50% of photolabile compound, even more preferably from 15% to about 30% of photolabile compound.

According to any embodiment of the invention, several gas-releasing photolabile compounds can be used simultaneously as mixtures, all of which can release the same type of gas or different types of gases.

It is believed that upon exposure to light, the photolabile compound generates a gas which, in non-diffusive capsules (as defined above), causes an increase in the internal pressure leading to the release of the oil phase. The increase in internal pressure might result in an extension or breaking of the microcapsule shell or wall. The extension (swelling) of the capsule shell should make the capsule more diffusive towards the outside and thus facilitate the release of the encapsulated oil phase. Depending on the chemical structure of the capsule shell and on the speed of gas formation, the extension of the capsule shell might finally lead to a complete breaking of the capsule shell and thus allow the oil phase to leak out. All these parameters can be easily optimized by a person skilled in the art considering the thickness of the walls its chemical nature and the loading of photolabile compound in the capsules as well as the desired speed of release.

Some photolabile compounds of formula (I) are commercially available, others can be prepared by generally known methods reported in the literature.

Photolabile compounds of formula (I) can be prepared as described in WO 99/60990, belonging to the present applicant. For example, photolabile compounds of formula (I) can be obtained by esterification of a 2-oxoacetic acid with a corresponding alcohol, by transesterification of 2-oxoacetates, such as the methyl or ethyl 2-oxoacetates, with a corresponding alcohol or even by Grignard reaction of a bromo-substituted hydrocarbon with a corresponding dialkyl oxalate. Alternatively, the photolabile compounds can also be obtained by oxidation of 2-hydroxyacetates or by a Friedel-Crafts reaction of an aryl derivative with a 2-chloro-2-oxoacetate in the presence of a Lewis acid.

The efficiency of generating a gas from said photolabile compound upon exposure to the light can be influenced by energy transfer via a photo-catalyst, said photo-catalyst can act via various mechanisms such as by photosensitation, photocatalysis or by photo-assisted catalysis. As defined by the International Union of Pure and Applied Chemistry (IUPAC) in Pure and Applied Chemistry, 2006, vol. 79, pages 293-465, the term "photosensitation" stands for a "photochemical or photophysical alteration occurring in one molecular entity as a result of initial absorption of radiation by another molecular entity called a "photosensitizer", "photocatalysis" means a "change in the rate of a chemical reaction or its initiation under the action of ultraviolet, visible, or infrared radiation in the presence of a substance—the photocatalyst—that adsorbs light and is involved in the chemical transformation of the reaction partners". Similarly, the term "photo-assisted catalysis" has been defined by the same source as a "catalytic reaction involving production of a catalyst by absorption of ultraviolet, visible or infrared radiation".

The component A. of the microcapsule according to the invention therefore optionally also comprises at least one photo-catalyst. The choice of a suitable photo-catalyst depends on the structure of the gas-generating photolabile compound and on the medium in which the photoreaction is supposed to take place. Said photo-catalysts are therefore of various chemical structures and are well known by a person skilled in the art; typical examples are easily found in the literature (e.g. M. Wainwright, "Photosensitizers in Biomedicine", John Wiley & Sons, Chichester, 2009, or G. K. Castello (Ed.), "Handbook of Photocatalysts: Preparation, Structure and Applications", Materials Science and Technologies Series, Nova Science Publishers, New York, 2010, or in other work of a similar nature, as well as in the abundant patent literature in the field of photosensitation or photocatalysis).

Non-limiting examples of compounds that might be suitable as photo-catalysts in some cases (e.g. for the use of α-ketoacids) comprise dyes, such as methylene blue, rose bengal, riboflavin or rhodamine B, as well as different forms of titanium dioxide.

Said photo-catalyst can be included in various amounts depending on its nature and the speed of release of the oil phase which is aimed. Typically, the microcapsules comprise, based on the total microcapsule weight, from about 0.01% to about 50% by weight, of photo-catalyst. Preferably the microcapsules comprise from about 1% to about 20% of photo-catalyst.

The component B. of the microcapsules according to the invention is an interfacial shell that can be obtained by a variety of processes.

According to any embodiment of the invention, said shell is based on aminoplast, polyamide, polyester, polyurea or polyurethane resins or a mixture thereof. Said resins and shells are well known to a person skilled in the art.

According to any embodiment of the invention, such a shell is preferably obtained by a phase separation process induced by polymerization, by interfacial polymerization, by coacervation or altogether. Such processes have been described in the prior art. Such a process can, for example, be based on amino resins produced by the polycondensation of an aldehyde (e.g. formaldehyde, 2,2-dimethoxyethanal, glyoxal, glyoxylic acid or glycolaldehyde and mixtures thereof) with an amine, namely urea, benzoguanamine, glycoluryl, melamine, methylol melamine, methylated methylol melamine, guanazole and the like, as well as mixtures thereof. Examples for suitable ureas are dimethylol urea, methylated dimethylol urea, urea-resorcinol, and mixtures thereof.

Some of the seminal literature related to encapsulation of perfumes by polycondensation of amino resins, namely melamine based resins, with aldehydes is represented by articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinency, which also address the suitable uses of such microcapsules, are represented for example by the article of H. Y. Lee et al. in Journal of Microencapsulation, 2002, vol. 19, pages 559-569, international patent publication WO 01/41915 or yet the article of S. Bone et al. in Chimia, 2011, vol. 65, pages 177-181.

The polycondensation of an aldehyde with an amine or an amino resin leads to shells or walls consisting of highly cross-linked resins known as thermoset resins (aminoplast resins). Suitable alkylolated polyamines for the microcapsules according to the invention encompass mixtures of mono- or polyalkylolated polyamines, which in turn may be partially alkylated with alcohols having from 1 to 6 methylene units, and also encompass mono- or polymethylolmelamine and/or mono- or polymethylolurea precondensates, such as those commercially available under the trademark Urac® (origin: Cytec Technology Corp.), Cymel® (origin: Cytec Technology Corp.), Urecoll® or Luracoll® (origin: BASF).

Other suitable amino resins from the mixtures of mono- or polyalkylolated polyamines can be obtained by polycondensation of an aldehyde such as 2,2-dimethoxyethanal, glyoxal, glyoxylic acid or glycolaldehyde and mixtures thereof, and an amine, as described in WO 2011/161618. Non-limiting examples of polyalkylolated polyamines from the polycondensation with 2,2-dimethoxyethanal comprise poly [N-(2,2-dimethoxy-1-hydroxy)] polyamines, mono- and di- [N-(2,2-dimethoxy)-1-hydroxy)] urea, mono-, di-, tri-, and/ or tetra-[N-(2,2-dimethoxy)-1-hydroxy)] melamine, tetra- [N-(2,2-dimethoxy)-1-hydroxy)]glycouryl or di-[N-(2,2-dimethoxy)-1-hydroxy)]benzoguanidine. Non-limiting examples of polyalkylolated polyamines from the polycondensation with glyoxal comprise poly[N-(2-hydroxyacetaldehyde)] polyamines, mono- and di-[N-(2-hydroxyacetaldehyde)] urea, mono-, di-, tri-, and/or tetra-[N-(2-hydroxyacetaldehyde)] melamine, tetra-[N-(2-hydroxyacetaldehyde)]glycouryl or di-[N-(2-hydroxyacetaldehyde)]benzoguanidine. Non-limiting examples of polyalkylolated polyamines from the polycondensation with glyoxylic acid comprise poly[N-(2-hydroxyacetic acid)] polyamines, mono- and di-[N-(2-hydroxyacetic acid)] urea, mono-, di-, tri-, and/or tetra-[N-(2-hydroxyacetic acid)] melamine, tetra-[N-(2-hydroxyacetic acid)]glycouryl or di-[N-(2-hydroxyacetic acid)]benzoguanidine. Non-limiting examples of polyalkylolated polyamines from the polycondensation with glycolaldehyde comprise poly[N-(ethane-1,2-diol)] polyamines, mono- and di-[N-(ethane-1,2-diol)] urea, mono-, di-, tri-, and/or tetra-[N-(ethane-1,2-diol)] melamine, tetra-[N-(ethane-1,2-diol)]glycouryl or di-[N-(ethane-1,2-diol)]benzoguanidine.

According to an embodiment of the invention, core-shell microcapsules are obtained by interfacial polymerization, in which the core is encapsulated into a crosslinked polyurea or polyurethane shell or wall formed by reaction of an amino resin, a polyamine or polyol with at least one polyisocyanate.

A polyurea microcapsule shell or wall is formed when a polyamine or an amino resin is used. Particularly efficient polyamines are water soluble guanidine salts and/or guanidine and/or amino resins such as those described above. By "water soluble guanidine salt" it is meant a salt soluble in water and resulting from the reaction of guanidine with an acid. One example of such salts is guanidine carbonate.

In the case where a polyol is used as the cross-linker, a polyurethane microcapsule shell or wall is formed. As polyol, glycerol is preferred.

The use of specific proportions of polyisocyanate versus polyamine or polyol is advantageous. Therefore, preferably, for each mole of isocyanate group, 1 to 10, preferably 2 to 5 moles of amine or alcohol groups are present. Accordingly, there is added an excess of the cross-linking agent.

When a polyisocyanate compound is reacted with an amino resin, e.g. obtained by a phase separation process as described above, a polyamine or a polyol, any polyisocyanate is suitable for the reaction, but a polyisocyanate comprising at least two isocyanate groups or at least three isocyanate groups is preferred. Low volatility polyisocyanate molecules are preferred because of their low toxicity. In particular, the polyisocyanate can advantageously be selected from the group consisting of a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate are even more preferred.

For the sake of clarity, by the expression "dispersion", in the present invention, it is meant a system in which particles are dispersed in a continuous phase of a different composition, and this term specifically includes a suspension or an emulsion.

A polymeric stabilizer can be used to prevent the microcapsules from agglomerating, thus acting as a protective colloid which is added to the monomer mixture, intended to form the shell, prior to polymerization. For the sake of clarity, in the present context by the expression "stabilizer", or similar, it is understood the meaning usual in the art, i.e. a compound that is capable of, or is added to, stabilize the system, e.g. to prevent aggregation or agglomeration of the microcapsules, for example in the consumer product application or during the process for the microcapsule preparation. The use of said stabilizer is standard knowledge to the person skilled in the art.

For the purpose of the present invention, said stabilizer can be an ionic or non-ionic surfactant or a colloidal stabilizer. The exact nature of such stabilizers is well known to a person skilled in the art. As non-limiting examples one may cite the following stabilizers: non-ionic polymers such as polyvinyl alcohol (Mowiol 18-88, Origin: Fluka), cellulose derivatives such hydroxyethyl cellulose or carboxymethyl cellulose such as Ambergum™ 1221 (origin: Aqualon Hercules), polyethylene oxide, co-polymers of polyethylene oxide and polyethylene or polypropylene oxide, co-polymers of alkyl acrylates and N-vinylpyrrolidone; ionic polymers such as acrylic copolymers of acrylamide and acrylic acid such as Alcapsol® 144 (origin: Ciba), e.g. acid/acrylamide copolymers produced from a monomer mixture of acrylic acid and acrylamide wherein the acrylic acid content is in the range of from 20 to 80%, acid anionic surfactants (such as sodium dodecyl sulfate), acrylic co-polymers bearing a sulfonate group (such as sodium poly(styrene sulfonate), and co-polymers of vinyl ethers and maleic anhydride.

Optionally, the microcapsules may be coated with a cationic copolymer. The cationic polymer allows partial or complete neutralization of the negative electrical charge borne by the microcapsules, or even the conversion of the negatively-charged microcapsules into positively-charged microcapsules. To this effect, according to the invention, preferred cationic polymers comprise cationic polyacrylates and acrylamides such as Salcare® SC60 (origin: BASF), cationic cellulose derivatives, such as those available under the trademark Ucare® (origin: Amerchol), and quaternized guar gums available under the trademark Jaguar® (origin: Rhodia). Other cationic compounds that can be used include the polyquaternium compounds, all which have a plurality of quaternary ammonium groups, or polymeric species such as diallyl dimethyl ammonium chloride/acrylamide polymers such as those available under the trade name Merquat® (origin: Nalco).

According to any embodiment of the invention, if the oil phase to be encapsulated by a polymerization process is hydrophobic (e.g. with the logarithm of its octanol/water partition coefficient (log P)>1, preferably >2), it will be included in the water-immiscible phase, whereafter the two phases are mixed by high shear mixing to form an oil-in-water emulsion. In this emulsion, the polymerization will take place at the interface between the two phases. Thus, the oil droplets will be surrounded by the microcapsule shell formed by the polymerization process.

According to any embodiment of the invention, the average size of the microcapsules may range between 1 micrometer to 100 micrometers, or even more, depending on the mixing shear stress applied to the system during microcapsule formation. The selection of the most appropriate range and distribution of size depends on the application for which the microcapsules are intended, and can be controlled and adjusted by the skilled person as a function of the latter. In a general manner the average size of the microcapsules according to the invention ranges between 1 micrometer and 600 micrometers and, more preferably, comprises a range of 1 to 200 micrometers.

The phase separation process induced by polymerization and the interfacial polymerization process described above essentially convert emulsions, consisting of a dispersed oil phase, containing the photolabile compound and, optionally, the photo-catalyst to be encapsulated and a continuous water phase, into a dispersion of solid beads consisting of a core surrounded by a shell, whose permeability depends on a number of factors, including the extent of cross-linking, and/or the thickness of the shell. A person skilled in the art is able to easily find optimal factors and conditions to obtain non-diffusive capsules as required by the present invention.

According to any embodiment of the invention, the invention's microcapsules obtained either by phase separation polycondensation or by interfacial polymerization have a shell thickness varying between 10 to 1000 nm, preferably between 20 and 500 nm, even more preferably between 25 and 350 nm. As an example, the capsule's shell thickness can be determined by atomic force microscopy (AFM) or scanning electron microscopy (SEM).

According to any embodiment of the invention, the microcapsules of the present invention may be characterized by a nominal shell to core mass ratio lower than 40%, preferably lower than 20% and, most preferably, lower than 10%, the invention thus providing thin and frangible shells that allow the diffusion of the fragrance molecules resulting from the degradation of the photolabile compound.

The nominal shell to core mass ratio depends on the amount of amino resin or polyamine or polyol and/or polyisocyanate used for the preparation of the microcapsules (and thus the shell thickness of the capsule) and which has a strong influence on the performance of the delivery system. An optimum value to reach a maximum of capsule stability and the best release performance has to be reached. Specific examples according to the invention are presented further on. As an example, the nominal shell to core mass ratio can vary from 0.4 to 0.01, preferably from 0.3 to 0.02, most preferably from 0.10 to 0.03.

The microcapsules of the present invention are provided in the form of aqueous slurries, having typically 20 to 55% of solid content, where the term "solid content" is relative to the total weight of the microcapsules. Alternatively, such slurries may be spray-dried in a generally known manner to provide powder products.

The slurry may contain formulation aids, such as stabilizing and viscosity control hydrocolloids, biocides, and, as the case may be, formaldehyde scavengers.

The aqueous phase can also advantageously comprise hydrophilic inorganic particles such as silica particles or titanium oxide, in order to adjust the density of the microcapsules. By doing so, the density of the microcapsules can be brought to a value similar to that of the end product into which it is intended to incorporate them and therefore the microcapsules are maintained homogeneously suspended and dispersed in such liquid products. This is particularly advantageous in perfuming microcapsules because the specific gravity of the perfuming ingredients is usually lower than 1 g/ml.

The microcapsules according to the invention protect the oil phase against premature degradation during storage in the application formulation and increase the deposition of the oil phase on the target substrate once the latter is treated with the consumer product.

According any embodiment of the invention, one may use the microcapsules of the present invention as a mixture with a free oil phase and/or with other microcapsules or other types of delivering technologies of the prior-art. Other microcapsules used in combination with those of the present invention can have a diffusive or non-diffusive shell.

Furthermore, the invention's microcapsules can also be advantageously used in all the fields of modern perfumery, i.e. fine or functional perfumery, to positively impart or modify the odor of a consumer product into which said invention's microcapsules are added. Consequently, another object of the present invention is represented by a perfuming consumer product comprising, i) as perfuming ingredient, at least one invention's microcapsule, as defined above; and ii) as an option a free perfume oil.

Such consumer product may be a solid or a liquid product. According to a particular embodiment, liquid products are preferred.

For the sake of clarity, by "free perfume oil" it is meant a perfume oil, e.g. as defined above, which is not encapsulated or part the invention microcapsules.

For the sake of clarity, by "consumer product" it is meant a consumer product which is typically perfumed and which is expected to deliver at least a perfuming effect, in other words it is a perfumed consumer product.

For the sake of clarity, it has to be mentioned that, by "perfuming consumer product" it is meant a consumer product which is expected to deliver at least a pleasant perfuming effect to the surface to which it is applied (e.g. skin, hair, textile, or hard surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of the microcapsules according to the present invention. It goes without saying that such a consumer product may also contain non-encapsulated perfume, i.e. perfume ingredients in free form.

The nature and type of the constituents of the consumer product do not warrant a more detailed description here, which in any case would not be exhaustive, the skilled person being able to select them on the basis of his general knowledge and according to the nature and the desired effect of said product.

Non-limiting examples of consumer products in which the microcapsules according to the invention can be used advantageously include perfumes, colognes or after-shave lotions; fabric care products, such as a liquid or solid detergents, fabric softeners or refreshers, ironing waters, tissues or other paper or cellulose based products such as nappies, and bleaches or home care products, including window and kitchen cleaners; body and hair care products (e.g. a shampoos, coloring preparations, conditioners and hair sprays), cosmetic preparations (e.g. creams, body deodorants or antiperspirants), or skin-care products (e.g. a perfumed soap, shower or bath mousse, oils or gels, or a hygiene product); an air care product, such as an air freshener or a "ready to use" powdered air freshener; or a home care product, such as a wipe, a dish detergent or hard-surface detergent.

As anticipated above, the invention's composition can be advantageously used for bringing a benefit to consumer products, such as its perfuming effect. Because some of the compounds of the oil phase described above can also have flavoring, cosmetic, skin caring, malodor counteracting, bactericide, fungicide, pharmaceutical, agrochemical, insect attractant or repellent properties, it is evident that the invention's microcapsules can also be used in formulations serving for flavoring, cosmetic, skin caring, malodor counteracting, bactericide, fungicide, pharmaceutical, agrochemical, insect attractant or repellent purposes. Indeed, said microcapsules, possess several other properties that make them particularly suitable for this purpose.

The proportions in which the microcapsules according to the invention can be incorporated into the various aforementioned consumer products vary within a wide range of values. These values are dependent on the nature of the article to be perfumed and on the desired organoleptic effect as well as the nature of the co-ingredients in a given consumer product. Typically, the consumer products comprise, based on the total consumer product weight, from about 0.01% to about 80% by weight, of microcapsules according to the present invention. Preferably the consumer products comprise from about 0.01% to about 30% of microcapsules. More preferably the consumer products comprise from about 0.1% to about 15% of microcapsules.

Formulations of consumer products, in which the microcapsules of the invention can be incorporated, can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO 2008/016684 (pages 10 to 14), in US 2007/0202063 (paragraphs [0044] to [0099]), in WO 2007/062833 (pages 26 to 44), in WO 2007/062733 (pages 22 to 40), in WO 2005/054422 (pages 4 to 9), in EP 1741775, in GB 2432843, in GB 2432850, in GB 2432851 or in GB 2432852.

Another object of the present invention is a method for intensifying or prolonging the effect of the characteristic fragrance of a perfume ingredient on a surface, characterized in that said surface is, preferentially in the presence of light, treated with a) a microcapsule of the invention, as defined above, containing an oil phase comprising at least one photolabile compound generating, upon exposure to the light, a gas selected among the group consisting of CO and $CO_2$, and, optionally, comprising at least one photo-catalyst; and b) a perfuming composition of the invention, as defined above, comprising the microcapsule of a); or c) a perfumed consumer product, as defined above, comprising the microcapsule of a); under conditions which are susceptible of allowing the release of the oil phase.

Suitable surfaces for such treatment are in particular textiles, hard surfaces, hair and skin.

A method to release a perfume from a microcapsule as defined above, characterized in that said microcapsule is exposed to conditions allowing the degradation of the photolabile α-ketoacid or α-ketoester of formula (I) with concomitant formation of a gas at a rate above $8.0 \times 10^{-5}$ $s^{-1}$, preferably above $1.0 \times 10^{-4}$ $s^{-1}$ is also an object of the invention.

Figure 1:
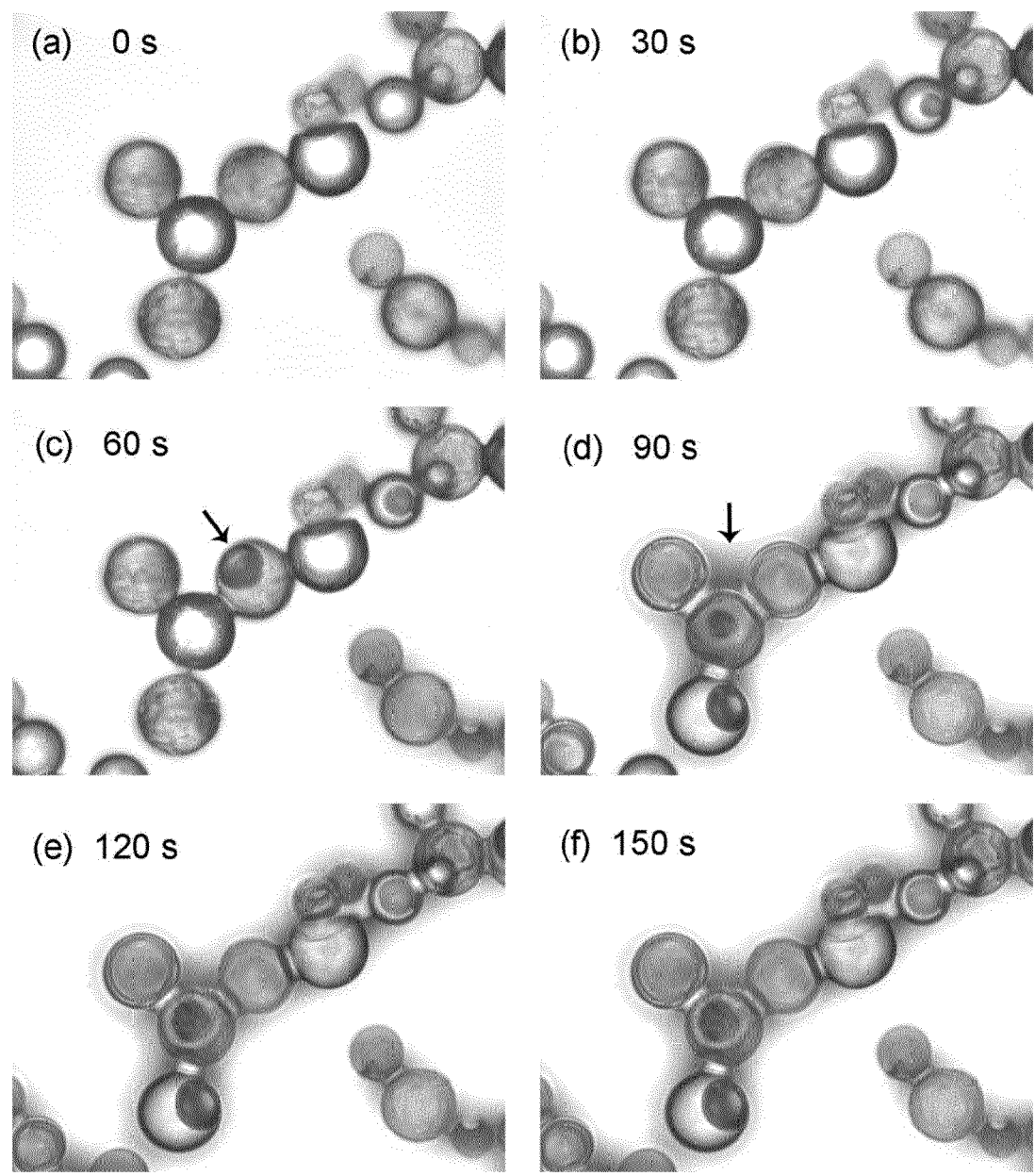
FIG. 1: Confocal microscope images of Microcapsules D according to the invention, prepared as described in Example 3b, containing Romascone® as the oil phase and ethyl 2-oxo-2-phenylacetate as an α-ketoester capable of generating a gas upon exposure to light. The first image (a) was taken before exposure to UVA-light, the others (b-f) after switching on the UVA-light. The images show the formation of the gas inside the capsules (e.g. arrow in image (c)), followed by the leakage of the oil phase out of the capsules (e.g. arrow in image (d)).
Figure 2:
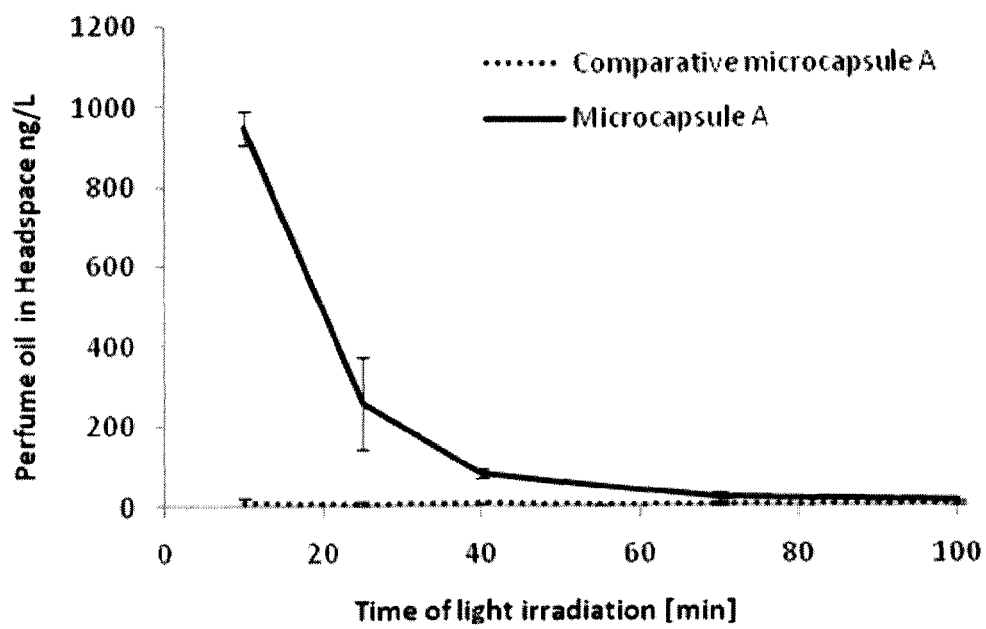
FIG. 2: Comparison of the amount of 4-tert-butylcyclohexyl acetate (perfume oil) released from Microcapsules A, prepared as described in Example 3a, containing an α-ketoester capable of generating a gas according to the invention (-) and from equivalent Comparative Microcapsules A without α-ketoester prepared as described in Comparative Example 3a) ( . . . ) as determined by dynamic headspace analysis after exposure of the microcapsules to light.
Figure 3:
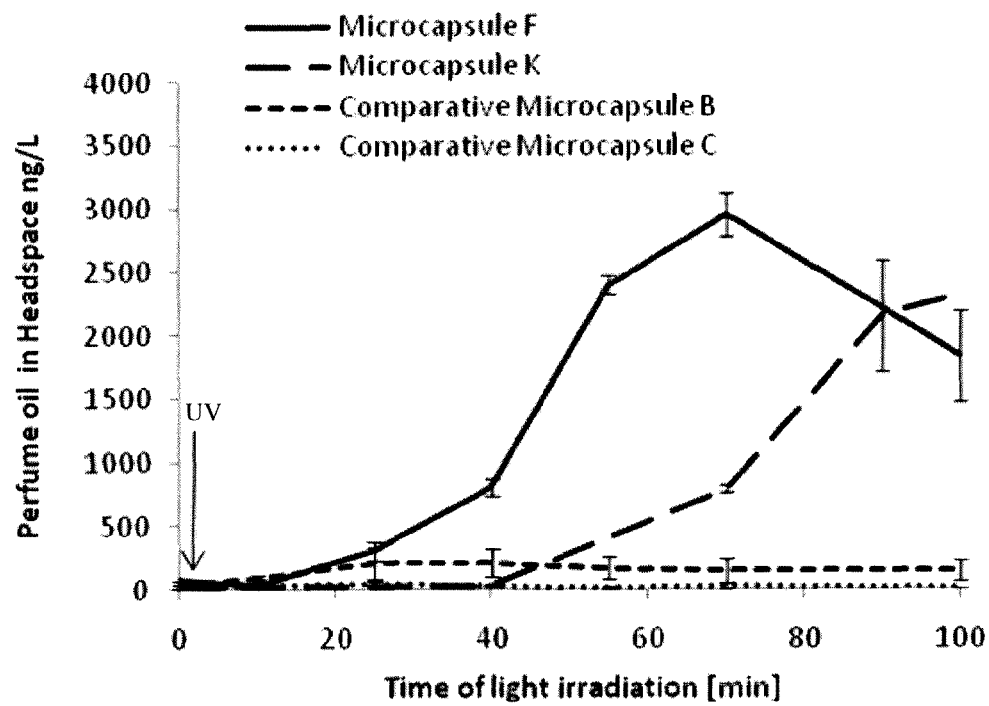
FIG. 3: Comparison of the amount of Romascone® (perfume oil) released from Microcapsules F, containing ethyl 2-oxo-2-phenylacetate, and K, containing ethyl 3-methyl-2-oxopentanoate, capable of generating a gas according to the invention and prepared as described in Examples 3b and 3c and the amount from equivalent prior-art Comparative Microcapsules B, containing phenethyl 2-oxo-2-phenylacetate, and C without α-ketoester and prepared as described in Comparative Examples 3b and 3c as determined by dynamic headspace analysis after exposure of the microcapsules to light.
Figure 4:
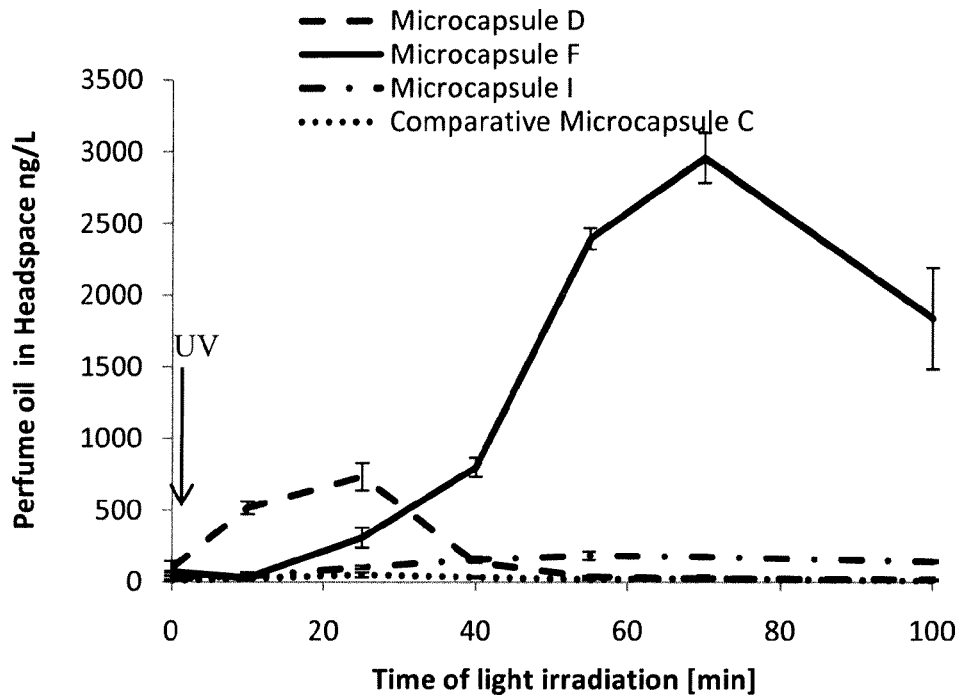
FIG. 4: Comparison of the amount of Romascone® (perfume oil) released from Microcapsules D (perfume oil/photolabile compound ratio=0.25), F (perfume oil/photolabile compound ratio=1), and I (perfume oil/photolabile compound ratio=3), containing ethyl 2-oxo-2-phenylacetate capable of generating a gas according to the invention and prepared as described in Example 3b and from equivalent prior-art Comparative Microcapsules C without α-ketoester and prepared as described in Comparative Example 3c as determined by dynamic headspace analysis after exposure of the microcapsules to light.
Figure 5:
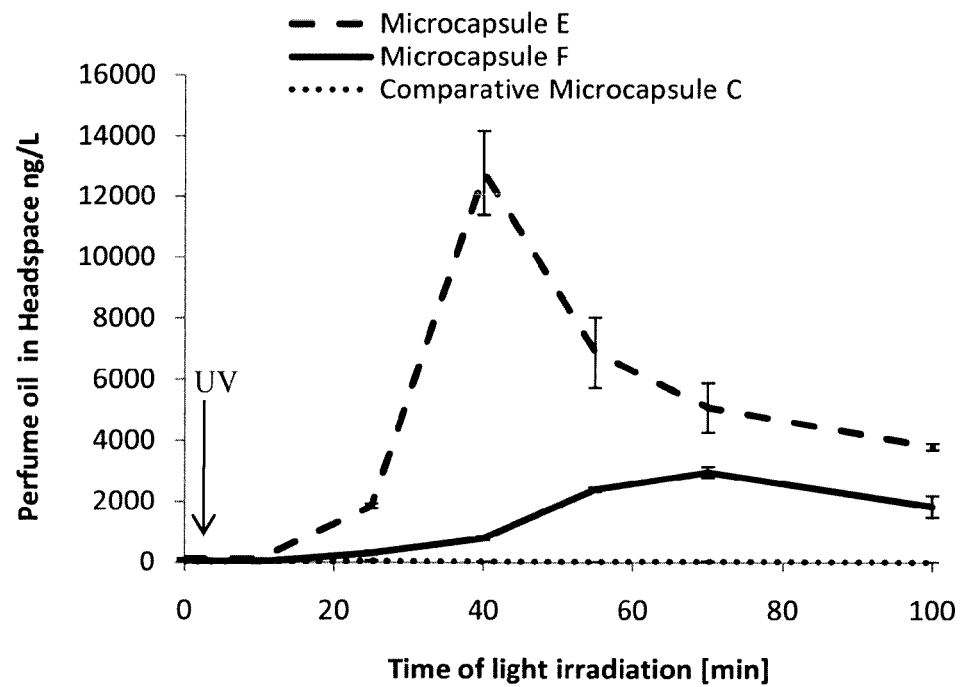
FIG. 5: Comparison of the amount of Romascone® (perfume oil) released from Microcapsules E (shell/oil phase ratio=0.16) and F (shell/oil phase ratio=0.24), containing ethyl 2-oxo-2-phenylacetate capable of generating a gas according to the invention and prepared as described in Example 3b and from equivalent prior-art Comparative Microcapsules C (shell/oil phase ratio=0.24) without α-ketoester and prepared as described in Comparative Example 3c as determined by dynamic headspace analysis after exposure of the microcapsules to light.
Figure 6:
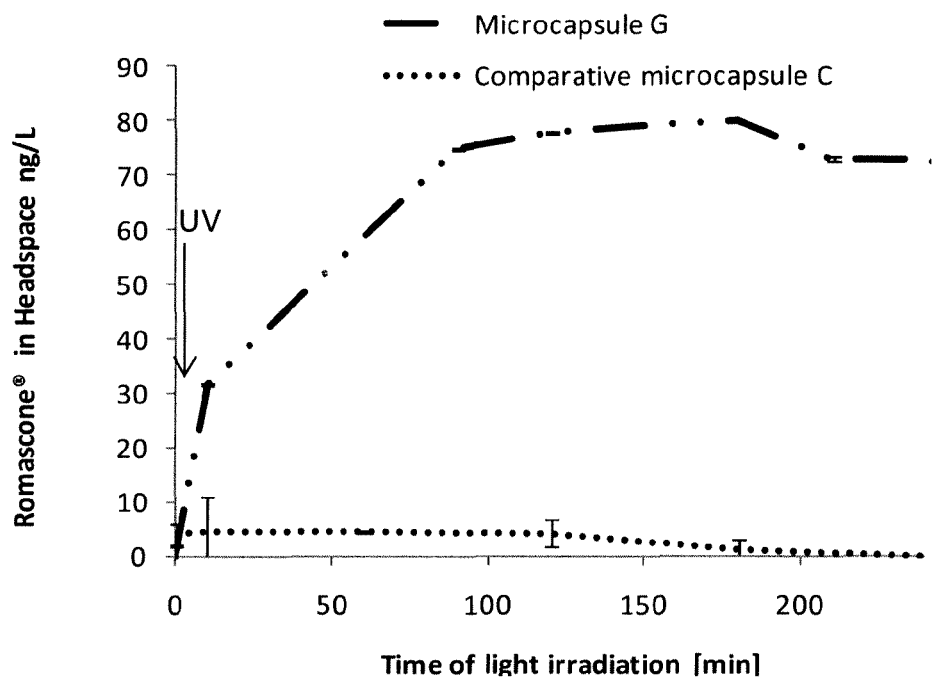
FIG. 6: Comparison of the amount of Romascone® (perfume oil) released from Microcapsules G (shell/oil phase ratio=0.32), containing ethyl 2-oxo-2-phenylacetate capable of generating a gas according to the invention and prepared as described in Example 3b and from equivalent prior-art Comparative Microcapsules C (shell/oil phase ratio=0.24) without α-ketoester and prepared as described in Comparative Example 3c as determined by dynamic headspace analysis after exposure of the microcapsules to light.
Figure 7:
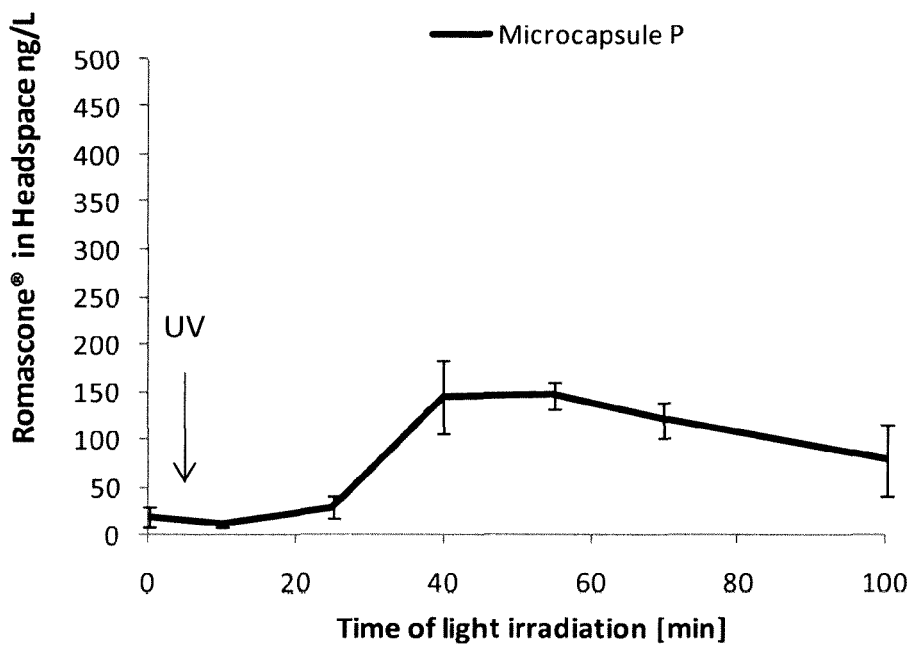
FIG. 7: Amount of Romascone® (perfume oil) released from Microcapsules P, containing ethyl 2-oxo-2-phenylacetate capable of generating a gas according to the invention and prepared as described in Example 3h.

The invention is now going to be illustrated by examples which should not be understood as limitative of the invention.

EXAMPLES

The invention is hereafter described in more detailed manner by way of the following examples, wherein the abbreviations have the usual meaning in the art, temperatures are indicated in degrees centigrade (° C.). NMR spectral data were recorded in CDCl$_3$ (if not stated otherwise) on a Bruker AMX 400 or 500 spectrometer in CDCl$_3$ at 400 or 500 MHz for $^1$H and at 100.6 or 125.8 MHz for $^{13}$C, the chemical displacements δ are indicated in ppm with respect to Si(CH$_3$)$_4$ as the standard, the coupling constants J are expressed in Hz (br.=broad peak). High performance liquid chromatography (HPLC) analyses were carried out on a Thermo Separation Products apparatus composed of a SpectraSystem SCM1000 online vacuum degasser, a SpectraSystem P4000 quaternary pump, a SpectraSystem AS3000 autosampler and a SpectraSystem UV6000LP diode array detector. Samples (10 μL) were eluted at 1 mL/min on a Macherey-Nagel Nucleosil® 120-5 C4 column (250×4 mm i.d.) with a gradient of water/acetonitrile (both containing 0.1% of trifluoroacetic acid) varying from 1:1 to 1:4 (during 5 min) and analyzed at 254 nm. Gas chromatography (GC) analyses were carried out on an Agilent Technologies 7890A GC System equipped with an Agilent Technologies 7683B Series Injector and a FID detector. Samples (5 μL, split ratio 50:1) were eluted at 2.4 mL/min with helium on an Agilent HP-5 capillary column (30 m, 0.32 mm i.d., film 0.25 μm) at 60° C. for 1 min, then to 200° C. at 20° C./min; the injector temperature was at 250° C., the detector temperature at 280° C. Commercially available reagents and solvents were used without further purification if not stated otherwise. Reactions were carried out in standard glassware under N$_2$.

Although specific conformations or configurations are indicated for some of the compounds, this is not meant to limit the use of these compounds to the isomers described. According to the invention, all possible conformation or configuration isomers are expected to have a similar effect.

Example 1

Preparation of α-Ketoesters Capable of Generating a Gas Upon Exposure to Light

Preparation of isopropyl 2-oxo-2-phenylacetate

A solution of 2-oxo-2-phenylacetic acid (16.21 g, 108 mmol), N,N-dimethylpyridin-4-amine (DMAP) (1.32 g, 10.8 mmol) and propan-2-ol (14.75 mL, 193.0 mmol) in dichloromethane (120 mL) was cooled on an ice-bath before a solution of N,N'-methanediylidenedicyclohexanamine (DCC) (26.41 g, 128.0 mmol) in dichloromethane (90 mL) was added during 1.5 h. The reaction mixture was stirred for 30 min at 0° C., then at 20° C. for 29 h. The precipitate formed in the reaction was filtered off and the filtrate taken up in ether, washed with water (3×), HCl 10%, (3×), and a saturated solution of Na$_2$CO$_3$ (2×). The organic layer was dried (Na$_2$SO$_4$) and concentrated. Column chromatography (SiO$_2$, heptane/ether 4:1) gave 17.40 g (84%) of a slightly yellow oil.

$^1$H-NMR (400 MHz): δ 8.02-7.97 (m, 2H); 7.68-7.62 (m, 1H); 7.55-7.48 (m, 2H); 5.33 (hept., J=6.3, 1 H); 1.41 (d, J=6.4, 6 H).

$^{13}$C-NMR (100.6 MHz): δ 186.72 (s); 163.66 (s); 134.80 (d); 132.58 (s); 129.96 (d); 128.89 (d); 70.67 (d); 21.74 (q).

Preparation of ethyl 2-oxo-2-(p-tolyl)acetate

Aluminum trichloride (14.47 g, 109 mmol) was suspended in dichloromethane (60 mL) at 0° C. before ethyl 2-chloro-2-oxoacetate (12.1 mL, 109 mmol) was added dropwise during 45 min. After stirring for 10 min, toluene (11.6 mL, 109 mmol) was added during 30 min and the mixture left warming to room temperature. After stirring for 1.5 h, the mixture was poured onto crushed ice (300 g) and concentrated hydrochloric acid (100 mL) and extracted with cyclohexane (100 mL). The organic layer was washed with sodium hydroxide (0.1 N, 100 mL) and a saturated aqueous solution of NaCl (2×80 mL), dried (MgSO$_4$) and concentrated to give 22.25 g of a yellow oil, still containing toluene.

$^{1}$H-NMR (500 MHz): δ 7.90 (d, J=8.3, 2H); 7.29 (d, J=8.0, 2H); 4.43 (q, J=7.2, 2H); 2.42 (s, 3H); 1.40 (t, J=7.1, 3H).
$^{13}$C-NMR (125.8 MHz): δ 186.11 (s); 164.07 (s); 146.22 (s); 130.16 (d); 130.08 (s); 129.63 (d); 62.20 (7); 21.89 (q); 14.12 (q).

Preparation of ethane-1,2-diyl bis(2-oxo-2-phenylacetate)

A solution of 2-oxo-2-phenylacetic acid (14.50 g, 96.5 mmol), DMAP (6.30 g, 51.5 mmol) and ethylene glycol (4.00 g, 64.4 mmol) in dichloromethane (75 mL) was cooled on an ice-bath before a solution of DCC (14.60 g, 71.0 mmol) in dichloromethane (50 mL) was added. Then more 2-oxo-2-phenylacetic acid (14.50 g, 96.5 mmol) in dichloromethane (20 mL), DMAP (6.30 g, 51.5 mmol) in dichloromethane (20 mL) and DCC (14.60 g, 71.0 mmol) in dichloromethane (35 mL) was added. The reaction mixture was left warming to room temperature and stirred for 6 h. The precipitate formed in the reaction was filtered off and washed with dichloromethane. The filtrate was washed with HCl 10%, (2×), a saturated solution of Na$_2$CO$_3$ (2×) and a saturated solution of NaCl (2×). The organic layer was dried (Na$_2$SO$_4$) and concentrated to give 18.80 g of the crude product. Column chromatography of 9.40 g (SiO$_2$, heptane/ethyl acetate 1:1) gave 7.16 g (89%) of a white solid.

$^{1}$H-NMR (400 MHz): δ 8.03-7.97 (m, 4H); 7.67-7.61 (m, 2H); 7.52-7.45 (m, 4H); 4.74 (s, 4H).
$^{13}$C-NMR (100.6 MHz): δ 185.55 (s); 163.26 (s); 135.13 (d); 132.19 (s); 130.10 (d); 128.99 (d); 62.99 (t).

Preparation of ethyl 2-oxopentanoate

A solution of 2-oxopentanoic acid (3.00 g, 25.8 mmol), ethanol (1.20 g, 25.8 mmol) and DMAP (0.32 g, 2.6 mmol) in dichloromethane (30 mL) was cooled with an ice bath before a solution of DCC (5.86 g, 28.4 mmol) in dichloromethane (15 mL) was added dropwise during 30 min. The reaction mixture was stirred for 10 min at 0° C., then at room temperature for 3 h. The precipitate formed during the reaction was filtered on a sintered glass frit and rinsed with dichloromethane (15 mL). The filtrate was concentrated under reduced pressure (40° C.) and the residue taken up in diethylether (100 mL). The organic phase was washed with water (3×30 mL), an aqueous solution of HCl (10%, 3×30 mL), water (30 mL), a saturated aqueous solution of NaHCO3 (3×30 mL) and water (30 mL). The aqueous phases were re-extracted with diethylether (100 mL). The combined organic phases were dried (Na$_2$SO$_4$) and concentrated under reduced pressure (45° C.). Bulb-to-bulb distillation (120° C., 8 mbar) gave 1.80 (45%) g of a colorless oil.

$^{1}$H-NMR (500 MHz): δ 4.32 (q, J=7.2, 2H), 2.82 (t, J=7.2, 2H), 1.67 (hex., J=7.4, 2H), 1.37 (t, J=7.2, 3H), 0.97 (t, J=7.5, 3H).
$^{13}$C-NMR (125.8 MHz): δ 194.67 (s), 161.32 (s), 62.35 (t), 41.14 (t), 16.54 (t), 14.03 (q), 13.52 (q).

Example 2

Degradation of α-Ketoacids and α-Ketoesters Capable of Generating a Gas Upon Exposure to Light α-Ketoacids or α-ketoesters according to the invention (0.08 mmol) were dissolved in acetonitrile (10 mL). The solutions (5 mL) were placed in a Pyrex® glass cell thermostatted at 25° C. (±1° C.) and exposed to UVA-light with a Sanalux SAN-40 lamp (origin: Sanalux GmbH) with 3.1 mW/cm$^2$ (at distance of ca. 15 cm from the lamp) for 120 min. The degradation of the compound was followed by HPLC and/or GC analysis (see above) at constant time intervals. Before irradiation (t$_0$) a first aliquot of the solution (50 µL) was pipetted off, diluted with acetonitrile (950 µL for HPLC analysis, 50 µL for GC analysis) and analyzed. Then the lamp was switched on, and further aliquots of the solutions were pipetted off (every 10 min during 2 h), diluted and analyzed as described above.

Observed first-order rate constants (k$_{obs}$) were obtained according to Equation 1 by plotting the negative natural logarithm of the (decreasing) peak areas measured at time t (A$_t$) over the one measured at time t$_0$ (A$_0$) against time.

$$A_t = A_0 e(-k_{obs}t) \qquad \text{(Eq. 1)}$$

Linear regression gave straight lines with good correlation coefficients (r$^2$). The measured rate constants are listed in Table 1.

TABLE 1

Observed first-order rate constants (k$_{obs}$) for the degradation of α-ketoacids and α-ketoesters according to the invention upon exposure to UVA-light (3.1 mW/cm$^2$) in acetonitrile at 25° C. (average data of at least two measurements).

| α-Ketoacid or α-ketoester | k$_{obs}$ [s$^{-1}$] | Method |
|---|---|---|
| 2-Oxo-2-phenylacetic acid (origin: Alfa Aesar) | 2.87 × 10$^{-4}$ | HPLC |
| Ethyl 2-oxo-2-phenylacetate (origin: Aldrich) | 7.87 × 10$^{-4}$ | HPLC |
| Isopropyl 2-oxo-2-phenylacetate | 7.20 × 10$^{-4}$ | HPLC |
| Ethyl 2-oxo-2-(p-tolyl)acetate | 4.11 × 10$^{-4}$ | HPLC |
| Ethane-1,2-diyl bis(2-oxo-2-phenylacetate) | 5.57 × 10$^{-4}$ | HPLC |
| Ethyl 2-oxopropanoate (origin: Acros) | 1.91 × 10$^{-4}$ | GC |
| Ethyl 2-oxopentanoate | 2.03 × 10$^{-4}$ | GC |
| Ethyl (±)-3-methyl-2-oxopentanoate (origin: Firmenich SA) | 3.10 × 10$^{-4}$ | GC |

Example 3

Preparation of Microcapsules According to the Present Invention Containing a Photolabile α-Ketoacid or α-Ketoester Capable of Generating a Gas Upon Exposure to Light and a Fragrance Molecule as the Oil Phase General Protocol for the Preparation of Polyurea Microcapsules of the Present Invention Containing a Photolabile α-Ketoacid or α-Ketoester:

In a beaker, a polyisocyanate (Desmodur® N100, Biuret of hexamethylene diisocyanate, origin: Bayer AG or Takenate® D-110N, Trimethylol propane-adduct of xylylene diisocyanate, origin Mitsui Chemicals) and the invention's photolabile α-ketoester were dissolved in the perfume oil (origin: Firmenich SA). The oil phase composed of the photolabile α-ketoester and the perfume oil was added to a solution of poly(vinyl alcohol) (PVOH) 18-88 (circa 0.42 g, origin: Aldrich) at 1 wt % in water (circa 42 mL). An emulsion was prepared by Ultra-Turrax stirring (model S25N 10G) between 15'000 and 24'000 rpm for 2 min. The droplet size was controlled by light microscopy. The emulsion was then introduced at room temperature into a 250 mL reactor and stirred with an anchor at 350 rpm. A solution of guanidine carbonate (origin: Aldrich) or guanazole (1H-1, 2,4-Triazole-3,5-diamine, origin: Alfa Aesar) in water (circa 5 mL) was added dropwise to the emulsion for 1 h. The reaction mixture was heated from room temperature to 70° C. during 1 h at the pH indicated below, then kept at 70° C. for 2 h, and finally cooled to room temperature to afford a white dispersion. Respective quantities are reported below.

a) Preparation of Microcapsules a According to the General Protocol

Microcapsules A were prepared with Desmodur® N100, ethyl 2-oxo-2-phenylacetate, 4-tert-butylcyclohexyl acetate (origin: Firmenich SA) and guanidine carbonate at pH 10.5.

TABLE 2

Composition of Microcapsules A

| Product | Quantity (g) |
| --- | --- |
| Desmodur ® N100 (a polyisocyanate) | 1.17 |
| Ethyl 2-oxo-2-phenylacetate (a photolabile α-ketoester) | 14.00 |
| 4-tert-Butylcyclohexyl acetate (a perfume oil) | 3.52 |
| PVOH 18-88 | 0.50 |
| Guanidine carbonate (a polyamine) | 0.4 |
| Water | 51.50 |
| Perfume oil/Photolabile compound ratio | 0.25 |
| Shell/Oil phase ratio | 0.09 | b) Preparation of Microcapsules B to J According to the General Protocol

Microcapsules B-J were prepared with Takenate® D-110N, ethyl 2-oxo-2-phenylacetate, Romascone® (methyl 2,2-dimethyl-6-methylene-1-cyclohexanecarboxylate, origin: Firmenich SA) or/and Hedione® HC (methyl 2-((1S,2R)-3-oxo-2-pentylcyclopentyl)acetate, origin: Firmenich SA), guanazole at pH 5.

TABLE 3

Composition of Microcapsules B to J

| Microcapsule | Takenate ® D-110N (a polyisoyanate) [g] | Guanazole (a polyamine) [g] | Ethyl 2-oxo-2-phenylacetate (a photolabile α-ketoester) [g] | Romascone ® (a perfume oil) [g] | Hedione ® HC (a perfume oil) [g] | PVOH 18-88 [g] | Water [g] | Perfume oil/Photolabile compound ratio | Shell/Oil phase ratio |
| --- | --- | --- | --- | --- | --- | --- | --- | --- | --- |
| B | 4.70 | 0.86 | 15.77 | 1.76 | — | 0.42 | 46.59 | 0.11 | 0.32 |
| C | 2.34 | 0.43 | 13.64 | 3.39 | — | 0.46 | 50.64 | 0.25 | 0.16 |
| D | 3.52 | 0.65 | 14.03 | 3.51 | — | 0.42 | 46.70 | 0.25 | 0.24 |
| E | 2.34 | 0.44 | 8.81 | 8.76 | — | 0.42 | 46.60 | 1 | 0.16 |
| F | 3.52 | 0.66 | 8.76 | 8.76 | — | 0.44 | 48.97 | 1 | 0.24 |
| G | 4.70 | 0.87 | 8.76 | 8.77 | — | 0.42 | 46.58 | 1 | 0.32 |
| H | 2.35 | 0.43 | 4.39 | 13.42 | — | 0.42 | 46.59 | 3 | 0.16 |
| I | 2.36 | 0.44 | 4.38 | 6.57 | 6.59 | 0.42 | 46.58 | 3 | 0.16 |
| J | 2.34 | 0.43 | 1.76 | 7.88 | 7.88 | 0.42 | 46.60 | 9 | 0.16 | c) Preparation of Microcapsules K According to the General Protocol

Microcapsules K were prepared with Takenate® D-110N, ethyl 3-methyl-2-oxopentanoate, Romascone®, Hedione® HC, and guanazole at pH 5.

TABLE 4

Composition of Microcapsules K

| Product | Quantity (g) |
| --- | --- |
| Takenate ® D-110N (a polyisocyanate) | 2.36 |
| Ethyl-3-methyl-2-oxopentanoate (a photolabile α-ketoester; origin: Firmenich SA) | 4.38 |
| Hedione ® HC (a perfume oil) | 6.59 |
| Romascone ® (a perfume oil) | 6.57 |
| PVOH 18-88 | 0.42 |
| Guanazole (a polyamine) | 0.44 |
| Water | 46.58 |
| Perfume oil/Photolabile compound ratio | 3 |
| Shell/Oil phase ratio | 0.16 | d) Preparation of Microcapsules L According to the General Protocol

Microcapsules L were prepared with Takenate® D-110N, ethyl 2-oxopropanoate, Romascone® and guanazole at pH 5.

TABLE 5

Composition of Microcapsules L

| Product | Quantity (g) |
| --- | --- |
| Takenate ® D-110N (a polyisocyanate) | 3.51 |
| Ethyl 2-oxopropanoate (a photolabile α-ketoester) | 8.76 |
| Romascone ® (a perfume oil) | 8.76 |
| PVOH 18-88 | 0.42 |
| Guanazole (a polyamine) | 0.66 |
| Water | 46.60 |
| Perfume oil/Photolabile compound ratio | 1 |
| Shell/Oil phase ratio | 0.24 | e) Preparation of Microcapsules M According to the General Protocol

Microcapsules M were prepared with Takenate® D-110N, 2-oxo-2-phenylacetic acid, Romascone® and guanazole at pH 5.

TABLE 6

Composition of Microcapsules M

| Product | Quantity (g) |
| --- | --- |
| Takenate ® D-110N (a polyisocyanate) | 3.51 |
| 2-Oxo-2-phenylacetic acid (a photolabile α-ketoacid) | 4.37 |
| Romascone ® (a perfume oil) | 13.13 |
| PVOH 18-88 | 0.42 |
| Guanazole (a polyamine) | 0.65 |
| Water | 47.12 |
| Perfume oil/Photolabile compound ratio | 3 |
| Shell/Oil phase ratio | 0.24 | f) Preparation of Microcapsules N According to the General Protocol

Microcapsules N were prepared with Takenate® D-110N, isopropyl 2-oxo-2-phenylacetate, Romascone® and guanazole at pH 5.

TABLE 7

Composition of Microcapsules N

| Product | Quantity (g) |
| --- | --- |
| Takenate ® D-110N (a polyisocyanate) | 3.51 |
| Isopropyl 2-oxo-2-phenylacetate (a photolabile α-ketoester) | 8.75 |
| Romascone ® (a perfume oil) | 8.75 |
| PVOH 18-88 | 0.42 |
| Guanazole (a polyamine) | 0.66 |
| Water | 46.63 |
| Perfume oil/Photolabile compound ratio | 1 |
| Shell/Oil phase ratio | 0.24 | g) Preparation of Microcapsules O Prepared with a Melamine-Formaldehyde Aminoplast Shell In a 250 mL Schmizo reactor, Urecoll SMV (Origin: BASF, 4.70 g), Alcapsol 144 (Origin: CIBA, 4.72 g) were dissolved in water (56.47 g) to give a colorless solution at pH 5.03 in the presence of acetic acid. Reaction mixture was stirred at room temperature for 1 h. A solution of Takenate® D-110N (0.62 g), ethyl 2-oxo-2-phenylacetate (11.02 g) and Romascone® (11.03 g) was added onto the aqueous solution. An emulsion was prepared by Ultra-Turrax stirring (model S25N 10G) at 13'500 rpm for 2 min. The droplet size was controlled by light microscopy. The emulsion was then introduced at room temperature into a 250 mL reactor and stirred with an anchor at 350 rpm. The reaction mixture was warmed up from room temperature to 90° C. during 1 h, and then kept at 90° C. for 3 h to afford a white dispersion.

h) Preparation of Microcapsules P Prepared with a Formaldehyde-Free Aminoplast Shell In a round bottom flask of 100 mL, oxalaldehyde (2.12 g), 2,2-dimethoxyacetaldehyde (1.71 g), 2-oxoacetic acid (0.74 g4), benzene-1,3,5-triamine (1.11 g) were dissolved in water (1.90 mL) at pH 9.44. Reaction mixture was stirred at 45° C. for 25 min and water (8.35 mL) was added at pH 9.3. Reaction mixture was added onto a solution of 1H-1,2,4-triazole-3,5-diamine (0.98 g) and Ambergum 1221 in solution at 2 wt % in water (33.2 g). A solution of ethyl 2-oxo-2-phenylacetate (10.51 g), Romascone® (10.51 g) with and Takenate® D-110N (2.65 g) was added onto the reaction mixture and an emulsion was prepared with an Ultra-Turrax stirrer (model S25N 10G) at 21'000 rpm at room temperature for 2 min. Emulsion was stirred at 60° C. for 4 h. Medium was slowly cooled to room temperature under stirring.

Comparative Example 3

Preparation of Comparative Microcapsules without a Photolabile α-Ketoacid or α-Ketoester (Capsules According to the Prior Art)

a) Preparation of Comparative Microcapsules A Corresponding to Microcapsules A without a Photolabile α-Ketoacid or α-Ketoester In a beaker, a polyisocyanate (Desmodur® N100, 1.17 g, 6.1 mmol) was dissolved in 4-tert-butylcyclohexyl acetate (18.00 g, 91.0 mmol). The oil phase with the fragrance was added to an aqueous solution of PVOH 18-88 (50 g, 1 wt % in water). An emulsion was prepared by Ultra-Turrax stirring (model S25N 10G) at 24'000 rpm for 2 min. The droplet size was controlled by light microscopy. The emulsion was then introduced at room temperature into a 250 mL reactor and stirred with an anchor at 350 rpm. A solution of guanidine carbonate (0.4 g, 4.4 mmol) in water (2 g) was added dropwise to the emulsion during 1 h. The reaction mixture was heated to 70° C. during 1 h, then kept at 70° C. for 2 h, and cooled to room temperature to afford a white dispersion.

b) Preparation of Comparative Microcapsules B Corresponding to Microcapsules F with a Photolabile Profragrance According to WO 2013/079435 Instead of a Photolabile α-Ketoacid or α-Ketoester Comparative Microcapsules B were prepared with Takenate® D-110N, phenethyl 2-oxo-2-phenylacetate, Romascone® and guanazole at pH 5, according to general protocol of Example 3.

TABLE 8

Composition of Comparative Microcapsules B

| Product | Quantity (g) |
| --- | --- |
| Takenate ® D-110N (a polyisocyanate) | 3.52 |
| Phenethyl 2-oxo-2-phenylacetate (a photolabile α-ketoester) | 8.75 |
| Romascone ® (a perfume oil) | 8.77 |
| PVOH 18-88 | 0.44 |
| Guanazole (a polyamine) | 0.66 |
| Water | 48.56 |
| Perfume oil/Photolabile compound ratio | 1 |
| Shell/Oil phase ratio | 0.24 | c) Preparation of Comparative Microcapsules C Corresponding to Microcapsules E without a Photolabile α-Ketoacid or α-Ketoester Comparative Microcapsules C were prepared with Takenate® D-110N, Hedione® HC, Romascone® and guanazole, according to the general protocol of Example 3.

TABLE 9

Composition of Comparative Microcapsules C

| Product | Quantity (g) |
| --- | --- |
| Takenate ® D-110N (a polyisocyanate) | 3.52 |
| Hedione ® HC (a perfume oil) | 8.75 |
| Romascone ® (a perfume oil) | 8.77 |
| PVOH 18-88 | 0.44 |
| Guanazole (a polyamine) | 0.65 |
| Water | 48.57 |
| Perfume oil/Photolabile compound ratio | 1 |
| Shell/Oil phase ratio | 0.24 |

Example 4

Release of the Oil Phase from the Microcapsules after Exposure to Light

Release of the Oil Phase from Microcapsules Containing a Photolabile α-Ketoester According to the Invention Upon Exposure to Light Followed by Confocal Microscopy To demonstrate the release of the oil phase from the microcapsules according to the invention upon exposure to light, a dispersion of Microcapsules D, obtained as described in Example 3b, were diluted with water (2×) and left decanting. The supernatant water phase was pipetted off, and the remaining microcapsule dispersion further diluted with water. This dispersion was then placed onto a glass slide and left drying for 2 h. The glass slide was examined on a confocal microscope (Leica DM RXE, equipped with a DFC300FX camera) using an image magnification of 1.6× and 40×. To localize the microcapsules on the glass slide white light was used. Then the UVA-light (340-380 nm) was switched on and photographs were taken at regular time intervals.

FIG. 1 displays typical photographs obtained for the irradiation of Microcapsules D. The first image (FIG. 1a) was taken before switching on UVA-light and shows the intact microcapsules. After exposure to UVA-light, one can see the formation of gas bubbles inside the capsules (as for example indicated by the arrow in FIG. 1c for one of the microcapsules), followed by the leakage of the oil phase out of the capsules (appearance of a gray shade in the background of the microcapsules, as for example indicated by the arrow in FIG. 1d).

Similar observations were made with a series of other microcapsules according to the present invention and prepared as described in Example 3.

Release of the Oil Phase from Microcapsules Containing a Photolabile α-Ketoester According to the Invention Upon Exposure to Light Followed by Dynamic Headspace Analysis Dispersions of microcapsules, obtained as described in Examples 3 and Comparative Examples 3, were diluted in water to have the same concentration of fragrance in the oil phase in all samples. An aliquot (0.1 to 0.2 g) of these dispersions was put onto a glass slide (aliquots where chosen to have the same amount of perfume on each experiment) and kept at room temperature in the dark for 24 h. The composition of these dispersions are listed in Table 10. The glass slide was then placed inside a headspace sampling cell (ca. 500 mL of inner volume), and exposed to a constant air flow of ca. 200 mL/min. The air was filtered through activated charcoal and aspirated through a saturated solution of NaCl to give a constant humidity of ca. 75%. Glass slides were kept in the dark and after 5 min the evaporated volatiles were adsorbed for 10 min onto a clean Tenax® cartridge (0.10 g). Then the glass slides were irradiated with xenon light (Heraeus Suntest CPS at about 45000 lux). The evaporated volatiles were adsorbed for 10 min onto a clean Tenax® cartridge (0.10 g) every 15 min. The cartridges were thermally desorbed on a Perkin Elmer TurboMatrix ATD thermodesorber, injected onto a Agilent Technologies 7890A gas chromatograph equipped with a HP-1 capillary column and eluted using a temperature gradient starting at 60° C. then heating to 200° C. at 15° C./min. The amount of fragrances released was quantified by external standard calibration.

The results obtained from the headspace analysis after irradiation of the different samples are summarized in FIGS. 2-7.

TABLE 10

Composition of the dispersions put onto the glass slides for headspace analysis

| Dispersion | Mass of dispersion [g] | Mass of water [g] | Concentration of volatile (wt %) |
| --- | --- | --- | --- |
| Comparative Microcapsules A (Comparative Example 3a) (Prior art) | 0.104 | 5.036 | 0.51 |
| Comparative Microcapsules B (Comparative Example 3b) (Prior art) | 0.100 | 5.200 | 0.50 |
| Comparative Microcapsules C (Comparative Example 3c) (Prior art) | 0.100 | 5.000 | 0.51 |
| Microcapsules A (Example 3a) | 0.518 | 4.724 | 0.49 |
| Microcapsules D (Example 3b) | 0.106 | 2.622 | 0.21 |
| Microcapsules E (Example 3b) | 0.100 | 5.000 | 0.51 |
| Microcapsules F (Example 3b) | 0.102 | 5.294 | 0.52 |
| Microcapsules G (Example 3b) | 0.100 | 5.000 | 0.50 |
| Microcapsules I (Example 3b) | 0.100 | 4.000 | 0.67 |
| Microcapsules K (Example 3c) | 0.109 | 5.003 | 0.56 |
| Microcapsules P (Example 3h) | 0.100 | 4.200 | 0.51 |

The data in FIGS. 2-7 clearly demonstrate that considerably higher headspace concentrations of perfume oil were measured in the headspace above microcapsules containing a photolabile α-ketoester according to the invention as compared to an equivalent prior art microcapsule. The presence of a gas-generating photolabile α-ketoester is thus suitable to efficiently trigger the release of an encapsulated oil phase without requiring scratching or rubbing of the microcapsules to mechanically break the shell.

Example 5

Release of the Oil Phase from the Microcapsules after Exposure to Light in an all Purpose Cleaner Application The use as perfuming ingredient of the present invention's microcapsules has been tested in an all purpose surface cleaner (APC). An APC formulation with the following final composition has been prepared:

| | |
|---|---|
| Neodol ® 91-8 (origin: Shell Chemicals) | 5.0% by weight |
| Marlon ® A 375 (origin: Huls AG) | 4.0% by weight |
| Sodium cumolsulphonate | 2.0% by weight |
| Kathon ® CG (origin: Rohm and Haas) | 0.2% by weight |
| Water | 88.8% by weight |

An aqueous dispersion of Microcapsules E according to the present invention (17.8 mg), prepared as described in Example 3b, containing Romascone® as the oil phase and ethyl 2-oxo-2-phenylacetate as the photolabile α-ketoester capable of generating a gas upon exposure to light, was weighed into the APC formulation (1 mL). Then the sample was diluted with demineralized tap water (9 mL). As the reference, another APC sample was prepared in the same way using an aqueous dispersion of Comparative Microcapsules C (17.8 mg), prepared as described in Comparative Example 3c, containing the same amount of Romascone® as Microcapsules E and Hedione® HC as the oil phase, but no photolabile α-ketoacid or α-ketoester capable of generating a gas. The two samples were vigorously shaken and then each deposited as a film onto a glass plate (ca. 4×10 cm) by carefully pipetting 0.75 mL of the diluted samples onto the surface of the substrate. The samples were then covered with a ca. 2.5 L crystallizing dish and left standing at room temperature in the dark. After one day, the substrates were each placed inside a headspace sampling cell (ca. 625 mL) and exposed to a constant air flow of ca. 200 mL/min. The air was filtered through active charcoal and aspirated through a saturated solution of NaCl (to ensure a constant humidity of the air of ca. 75%). The headspace sampling cells were placed inside the xenon lamp (described above). Without switching on the lamp, the volatiles were adsorbed onto a waste Tenax® cartridge during 5 min, then onto a clean Tenax® cartridge during 10 min. Then the lamp was switched on and the samples were exposed to xenon light at about 45000 lux. The volatiles were adsorbed onto a clean Tenax® cartridge during 10 min and onto a waste Tenax® cartridge during 5 min. This sequence was repeated 3 times. Then the volatiles were adsorbed onto a clean Tenax® cartridge during 10 min and onto a waste Tenax® cartridge during 20 min. This sequence was repeated twice. A total of eight data points was collected (the first one without exposure to light; the seven other ones upon continuous exposure to xenon light). The waste cartridges were discarded; the others were desorbed on a Perkin Elmer TurboMatrix ATD 350 thermodesorber coupled to an Agilent Technologies 7890A GC System equipped with a HP-5 MS capillary column (30 m, i.d. 0.25 mm, film 0.25 μm) and an Agilent Technologies 5975C Series GC/MSD quadrupole mass spectrometer. The amount of Romascone® in the headspace was quantified by GC/MS by eluting the volatiles with a two step temperature gradient starting at 60° C. for 1 min, then going to 200° C. at 15° C./min and to 260° C. at 25° C./min and by using selected ion monitoring. Headspace concentrations (in ng/L air) were obtained by external standard calibrations of Romascone® using ethanol solutions of five different concentrations and injecting 0.2 μL of the calibration solutions onto clean Tenax® cartridges, which were immediately desorbed under the same conditions as those resulting from the headspace sampling. All measurements were performed at least twice.

The headspace concentrations of Romascone® measured above the glass plates are listed in Table 11.

TABLE 11

Headspace concentrations of Romascone ® released from microcapsules in the dark and after the exposure to xenon light (at 45000 lux) in an APC application on glass.

| Datapoint N° | After exposure to | Headspace concentration of Romascone ® released from Comparative Microcapsules C containing Romascone ® and Hedione ® HC and no photolabile α-ketoester [ng/L] of air | Headspace concentration of Romascone ® released from Microcapsules E containing Romascone ® and ethyl 2-oxo-2-phenylacetate as the photolabile α-ketoester [ng/L] of air |
|---|---|---|---|
| 1 | Dark (15 min) | 77.3 | 11.7 |
| 2 | Light (10 min) | 40.3 | 5.7 |
| 3 | Light (25 min) | 12.1 | 348.2 |
| 4 | Light (40 min) | 14.9 | 1285.8 |
| 5 | Light (55 min) | 25.9 | 1672.5 |
| 6 | Light (70 min) | 24.3 | 1052.2 |
| 7 | Light (100 min) | 23.9 | 486.2 |
| 8 | Light (130 min) | 18.9 | 153.7 |

After 40 min of irradiation with xenon light, about 85 times more Romascone® was released into the headspace above the microcapsules according to the invention as compared to the reference sample. These data clearly demonstrate that considerably higher headspace concentrations of Romascone® can be released by using a photolabile α-ketoester capable of generating a gas and exposing the sample to light as compared to a reference microcapsule without photolabile α-ketoester. Furthermore, the release of the oil phase from the microcapsules according to the present invention does not require a mechanical breakage of the microcapsules, typically obtained by rubbing or scratching the capsules. The microcapsules according to the present invention are thus suitable to increase the amount of fragrance released from an all purpose cleaner formulation on hard surfaces.

Example 6

Release of the Oil Phase from the Microcapsules after Exposure to Light in a Fabric Softener Application The use as perfuming ingredient of the present invention's microcapsules has been tested in a fabric softener. A fabric softener formulation with the following final composition was used:

| | |
|---|---|
| Stepantex ® VL90 A (origin: Stepan) | 16.5% by weight |
| Calcium chloride (10% aq. solution) | 0.6% by weight |
| Water | 82.9% by weight |

An aqueous dispersion of Microcapsules E according to the present invention (150.9 mg), prepared as described in Example 3b, containing Romascone® as the oil phase and ethyl 2-oxo-2-phenylacetate as the photolabile α-ketoester capable of generating a gas upon exposure to light, and water (1 mL) were added to the above mentioned fabric softener formulation (1.8 g). As the reference, another fabric softener sample was prepared in the same way using an aqueous dispersion of Comparative Microcapsules C (150.3 mg), prepared as described in Comparative Example 3c, containing the same amount of Romascone® as Microcapsules E and Hedione® HC as the oil phase, but no photolabile α-ketoacid or α-ketoester capable of generating a gas.

After homogenization, the samples were dispersed in a beaker with 600 mL of demineralized cold tap water. An aliquot of the dispersions (4 g) were each pipetted onto the surface of a standard cotton sheet (EMPA cotton test cloth Nr. 221, origin: Eidgenossische Materialprüfanstalt (EMPA), pre-washed with an unperfumed detergent powder and cut to ca. 12×12 cm sheets). The cotton sheets were line-dried for one day in the dark and then each put inside a headspace sampling cell (ca. 160 mL). The headspace sampling cells were placed inside the xenon lamp (described above), thermostatted at 25° C. and exposed to a constant air flow of ca. 200 mL/min. The air was filtered through active charcoal and aspirated through a saturated solution of NaCl (to ensure a constant humidity of the air of ca. 75%). The volatiles were sampled and analyzed as described above (Example 5). The measurements were performed in duplicate.

The headspace concentrations of Romascone® measured above the cotton sheets are listed in Table 12.

TABLE 12

Headspace concentrations of Romascone ® released from microcapsules in the dark and after the exposure to xenon light (at 45000 lux) in a fabric softener formulation on cotton.

| Datapoint N° | After exposure to | Headspace concentration of Romascone ® released from Comparative Microcapsules C containing Romascone ® and Hedione ® HC and no photolabile α-ketoester [ng/L] of air | Headspace concentration of Romascone ® released from Microcapsules E containing Romascone ® and ethyl 2-oxo-2-phenylacetate as the photolabile α-ketoester [ng/L] of air |
|---|---|---|---|
| 1 | Dark (15 min) | 442.1 | 183.8 |
| 2 | Light (10 min) | 184.6 | 81.8 |
| 3 | Light (25 min) | 120.1 | 69.1 |
| 4 | Light (40 min) | 62.7 | 87.3 |
| 5 | Light (55 min) | 24.1 | 82.4 |
| 6 | Light (70 min) | 14.7 | 66.7 |
| 7 | Light (100 min) | 8.3 | 51.7 |
| 8 | Light (130 min) | 5.2 | 42.2 |

The data show that less Romascone® was released from Microcapsules E containing the photolabile α-ketoester as compared to the Comparative Microcapsules C without photolabile α-ketoester when the sampling was performed in the dark (Datapoint 1). After switching on the light, a long-lasting effect of Romascone® release was observed for the sample containing Microcapsules E according to the invention with respect to the reference. Higher headspace concentrations of Romascone® were measured after exposure of the microcapsules to light for 40 min (Datapoint 4). After exposure to light for 130 min (Datapoint 8) about 8 times more Romascone® was released from Microcapsules E according to the invention then from the reference. The microcapsules according to the present invention are thus suitable to increase the amount of fragrance released from a fabric softener formulation on textiles.

What is claimed is:
1. A non-diffusive microcapsule comprising;
   A. a core comprising:
      an oil phase;
      at least one photolabile α-ketoacid or α-ketoester capable of generating, upon exposure to light a gas of CO or $CO_2$ and being of formula

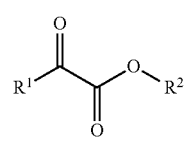

(I)

wherein $R^1$ represents:
      i) a $C_{1-16}$ hydrocarbon group optionally comprising one to four oxygen, sulphur or nitrogen atoms, provided that no heteroatom is directly connected to the CO group; or
      ii) a group of formula $R^{1'}(CO\text{—}COOR^2)_n$ wherein $R^2$ has the same meaning as below and $R^{1'}$ is a $C_{2-10}$ hydrocarbon group, optionally comprising one or two oxygen or nitrogen atoms, provided that no heteroatom is directly connected to the CO group, wherein $R^{1'}$ is linked to the keto functional group of the α-ketoacid or α-ketoester and wherein n is an integer comprised between 1 and 4;

and wherein $R^2$ represents either a hydrogen atom or an alkaline metal ion, or a primary or secondary group which is:
      a) a $C_{1-4}$ hydrocarbon group optionally comprising one or two oxygen or nitrogen atoms; or
      b) a $C_{5-22}$ hydrocarbon group optionally comprising one to ten oxygen atoms or one to two nitrogen atoms; provided that said $C_{5-22}$ hydrocarbon group is such as that the corresponding aldehyde or ketone of the O—$R^2$ moiety is an odorless compound; or
c) a group of formula $R^{2'}(OOC—CO—R^1)$, wherein $R^1$ has the same meaning as above and $R^{2'}$ is a $C_{2-12}$ hydrocarbon group optionally comprising one to six oxygen atoms and wherein $R^{2'}$ is linked to the ester functional group of the α-ketoester, and wherein n is an integer comprised between 1 and 4;
provided that at least one of $R^1$ or $R^2$ is a group as defined in i) or a) or b) respectively; and
optionally comprising at least one photo-catalyst; and
B. a shell surrounding said core formed by interfacial polymerization or by a phase separation process induced by polymerization or by coacervation;
wherein the amount of gas generated upon exposure to light is sufficient to expand and break the shell to release the oil from the capsule.

2. A microcapsule according to claim 1, characterized in that it comprises, based on the total microcapsule weight, from about 20% to about 96% of oil phase.

3. A microcapsule according to claim 1, characterized in that $R^1$ represents:
i) a $C_{1-10}$ hydrocarbon group optionally comprising one or two oxygen, sulphur or nitrogen atoms, provided that no heteroatom is directly connected to the CO group; or
ii) a group of formula $R^{1'}(CO—COOR^2)_n$ wherein $R^2$ has the meaning set in claim 1; $R^{1'}$ is a $C_{2-6}$ hydrocarbon group and n is equal to 1 or 2.

4. A microcapsule according to claim 1, characterized in that $R^2$ represents a hydrogen atom or a primary or secondary group which is:
a) a $C_{2-4}$ hydrocarbon group optionally comprising one or two oxygen or nitrogen atoms; or
b) a $C_{5-16}$ hydrocarbon group optionally comprising one to seven oxygen atoms or one or two nitrogen atoms; provided that said $C_{5-16}$ hydrocarbon group is such as that the corresponding aldehyde or ketone of the O—$R^2$ moiety is an odorless compound; or
c) a group of formula $R^{2'}(OOC—CO—R^1)_n$ wherein $R^1$ has the meaning set in claim 1 and $R^{2'}$ is a $C_{2-6}$ hydrocarbon group optionally comprising one or two oxygen atoms and n is equal to 1 or 2.

5. A microcapsule according to claim 1, characterized in that said α-ketoacid or α-ketoester generates a gas upon exposure to light at a wavelength comprised between 450 and 320 nm.

6. A microcapsule according to claim 1, characterized in that it comprises, based on the total microcapsule weight, from 10% to 50% of photolabile α-ketoacid or α-ketoester.

7. A microcapsule according to claim 1, characterized in that the shell surrounding said core is an aminoplast, polyamide, polyester, polyurea or polyurethane resin or a mixture thereof.

8. A microcapsule according to claim 1, characterized in that said shell has a thickness varying between 20 and 500 nm.

9. A microcapsule according to claim 1, characterized in that the oil phase comprises a perfuming oil.

10. A perfuming consumer product comprising:
i) as perfuming ingredient, at least one microcapsule as defined in claim 9; and
ii) as an option a free perfume oil.

11. A perfuming consumer product according to claim 10, characterized in that the consumer product is a perfume, a fabric care product, a body-care product, an air care product or a home care product.

12. A perfuming consumer product according to claim 10, characterized in that the consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

13. A method to release a perfume from a microcapsule as defined in claim 9, characterized in that said microcapsule is exposed to conditions allowing the degradation of the photolabile α-ketoacid or α-ketoester of formula (I) with concomitant formation of a gas at a rate above $8.0\times10^{-5}$ $s^{-1}$ in order to break the shell to release the oil from the capsule.

14. A method to release a perfume from a microcapsule as defined in claim 9, characterized in that said microcapsule is exposed to conditions allowing the degradation of the photolabile α-ketoacid or α-ketoester of formula (I) with concomitant formation of a gas at a rate above $1.0\times10^{-4}$ $s^{-1}$ in order to break the shell to release the oil from the capsule.

15. A non-diffusive microcapsule comprising:
A. a core comprising:
an oil phase;
at least one photolabile α-ketoacid or α-ketoester capable of generating, upon exposure to light a gas of CO or $CO_2$ and being of formula $$R^1-\underset{O}{\underset{\|}{C}}-\underset{O}{\underset{\|}{C}}-O-R^2 \tag{I}$$

wherein $R^1$ represents:
i) a $C_{1-16}$ hydrocarbon group optionally comprising one to four oxygen, sulphur or nitrogen atoms, provided that no heteroatom is directly connected to the CO group; or
ii) a group of formula $R^{1'}(CO—COOR^2)_n$ wherein $R^2$ has the same meaning as below and $R^{1'}$ is a $C_{2-10}$ hydrocarbon group, optionally comprising one or two oxygen or nitrogen atoms, provided that no heteroatom is directly connected to the CO group, wherein $R^{1'}$ is linked to the keto functional group of the α-ketoacid or α-ketoester and wherein n is an integer comprised between 1 and 4;
and wherein $R^2$ represents either a hydrogen atom or an alkaline metal ion, or a primary or secondary group which is:
a) a $C_{1-4}$ hydrocarbon group optionally comprising one or two oxygen or nitrogen atoms; or
b) a $C_{5-22}$ hydrocarbon group optionally comprising one to ten oxygen atoms or one to two nitrogen atoms; provided that said $C_{5-22}$ hydrocarbon group is such as that the corresponding aldehyde or ketone of the O—$R^2$ moiety is an odorless compound; or
c) a group of formula $R^{2'}(OOC—CO—R^1)$, wherein $R^1$ has the same meaning as above and $R^{2'}$ is a $C_{2-12}$ hydrocarbon group optionally comprising one to six oxygen atoms and wherein $R^{2'}$ is linked to the ester functional group of the α-ketoester, and wherein n is an integer comprised between 1 and 4;
provided that at least one of $R^1$ or $R^2$ is a group as defined in i) or a) or b) respectively; and from 1% to 20% of at least one photo-catalyst based on the total microcapsule weight; and B. a shell surrounding said core formed by interfacial polymerization or by a phase separation process induced by polymerization or by coacervation.

* * * * *